US 10,772,870 B2

United States Patent
Nebolsin et al.

(10) Patent No.: US 10,772,870 B2
(45) Date of Patent: *Sep. 15, 2020

(54) BISAMIDE DERIVATIVE OF DICARBOXYLIC ACID AS AN AGENT FOR STIMULATING TISSUE REGENERATION AND RECOVERY OF DIMINISHED TISSUE FUNCTION

(71) Applicant: TREAMID THERAPEUTICS GmbH, Berlin (DE)

(72) Inventors: Vladimir Evgenievich Nebolsin, Moskovskaya Obl. (RU); Anastasia Vladimirovna Rydlovskaya, St. Petersburg (RU); Alexandr Mikhailovich Dygai, Tomsk (RU); Tatiana Gennadievna Borovskaya, Tomsk (RU); Evgenii Germanovich Skurikhin, Tomsk (RU)

(73) Assignee: Treamid Therapeutics GmbH, Berlin (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/103,264

(22) Filed: Aug. 14, 2018

(65) Prior Publication Data

US 2018/0353479 A1 Dec. 13, 2018

Related U.S. Application Data

(63) Continuation of application No. 15/576,387, filed as application No. PCT/RU2016/050015 on May 26, 2016, now Pat. No. 10,076,511.

(30) Foreign Application Priority Data

May 27, 2015 (RU) .................. 2015120055

(51) Int. Cl.

| | | |
|---|---|---|
| *A61K 31/417* | (2006.01) | |
| *A61P 31/20* | (2006.01) | |
| *A61P 3/08* | (2006.01) | |
| *A61P 19/04* | (2006.01) | |
| *A61K 31/16* | (2006.01) | |
| *A61P 11/00* | (2006.01) | |
| *A61P 1/18* | (2006.01) | |
| *A61K 31/4164* | (2006.01) | |
| *A61P 15/08* | (2006.01) | |

(52) U.S. Cl.
CPC ............ *A61K 31/417* (2013.01); *A61K 31/16* (2013.01); *A61K 31/4164* (2013.01); *A61P 1/18* (2018.01); *A61P 3/08* (2018.01); *A61P 11/00* (2018.01); *A61P 15/08* (2018.01); *A61P 19/04* (2018.01); *A61P 31/20* (2018.01)

(58) Field of Classification Search
CPC .. A61K 31/417; A61K 31/16; A61K 31/4164; A61P 19/04; A61P 3/08; A61P 31/20; A61P 1/18; A61P 11/00; A61P 15/08

USPC .......................................................... 514/397
See application file for complete search history.

(56) References Cited

U.S. PATENT DOCUMENTS 10,076,511 B2 * 9/2018 Nebolsin ................ A61K 31/16

FOREIGN PATENT DOCUMENTS

WO    2014/168523 A1    10/2014

OTHER PUBLICATIONS

2004—Svartberg J., von Mühlen D., Sundsfjord J., et al. "Waist circumference and testosterone levels in community dwelling men. The Tromsø study" European Journal of Epidemiology. 2004. vol. 19(7). p. 657-667.
Mar. 2013—Minami K., Seino S. Current status of regeneration of pancreatic ?-cells. Journal of Diabetes Investigation. vol. 4, Issue 2. pp. 131-141.
2010—Jung Y1, Witek RP, Syn WK. Signals from dying hepatocytes trigger growth of liver progenitors// Gut.—vol. 5. p. 555-65.
2001—Johri A.M., Heaton J. P., Morales A. Severe erectile dysfunction is a marker for hyperprolactinemia // Int J Import Res. vol. 13 No. 3. p. 176-82.
2000—Meczekalski B., Tonetti A., Monteleone R. et al. Hypothalamic amenorrhea with normal body weight: ACTH, allopregnanolone and cortisol responses to corticotrophin-releasing hormone test // Eur. J. Endocrinol.—V.142. —R. 280-285.

(Continued)

*Primary Examiner* — Yong L Chu
(74) *Attorney, Agent, or Firm* — Banner & Witcoff, Ltd.

(57) ABSTRACT

The invention relates to the field of medicine and concerns an agent that stimulates tissue regeneration and the recovery of diminished tissue and organ function. A medicinal agent for the treatment and/or prophylaxis of a pathological condition selected from the group including metabolic syndrome, impaired glucose tolerance, hepatitis, particularly chronic hepatitis and toxic hepatitis, idiopathic pulmonary fibrosis (IPF), emphysema of the lungs, chronic obstructive pulmonary disease (COPD) and cachexia, particularly as a result of impaired glucose tolerance, pulmonary fibrosis, chronic obstructive pulmonary disease, cancer and other diseases, is proposed in the form of an agent based on Treamide. The latter is a bisamide derivative of dicarboxylic acid of formula (I) or a pharmaceutically acceptable salt thereof.

(I)

8 Claims, 5 Drawing Sheets

(56) References Cited

OTHER PUBLICATIONS

2003—Bhasin S., Taylor W.E., Singh R. et al. The mechanisms of androgen effects on body composition: mesenchymal pluripotent cell as the target of androgen action. J Gerontol Med Sci 2003; 58A:M1103-1110.

1999—"Differentiation of Murine Premigratory Primordial Germ Cells in Culture" A.J. Richards, G.C.Enders, J.L Resnick // Biol. Reprod.—vol. 61.—p. 1146-1151.

2009—Exercise intolerance and systemic manifestations of pulmonary emphysema in a mouse model Lüthje L., Raupach T., Michels H. et al. // Respiratory Research 2009, 10: 7.

2015—Susumu Sato, Erzsebet Bartolák-Suki, Harikrishnan Parameswaran, Hiroshi Hamakawa1 and Béla Suki. "Scale dependence of structure-function relationship in the emphysematous mouse lung" Front. Physiol. 6:146. doi: 10.3389/fphys.2015.00146.

2015—Yu-Chou T., Samuel K.K., I-Lu L. et al. "Preclinical Investigation of the Novel Histone Deacetylase Inhibitor AR-42 in the Treatment of Cancer-Induced Cachexia" JNCI J Natl Cancer Inst (2015) 107(12)).

1993—Podyminiogin M.A. et al., Synthenitc RNA-cleaving molecules mimicking ribonuclease A active center. Design and cleavage of tRNA transcripts. Nucleic Acids Research , 1993, vol. 21, No. 25, pp. 5950-5956.

2012—Hoizumi M. et al. Diabetes treatment with the aim of blood glucose normalization.Nihon Rinsho., 2012, vol. 70, No. 8, p. 1445-1450, abstract, [on-line], Retrieved form PubMed, PMID: 22894087.

Sep. 8, 2016—International Search Report—PCT/RU2016/050015.

2014—Publication; Updated Mar. 2013, A. Jungwith, et al., "Guidelines on Male Infertility" pp. 8 and 35.

Oct. 4, 2012—Munoz-Barrutia et al., "Quantification of Lung Damage in an Elastase-Induced Mouse Model of Emphysema" International Journal of Biomedical Imaging. vol. 2012, Article ID 734734, 11 pages.

Sep. 2000—Bayne et al., "The Selectivity and Specificity of the Actions of the Lipido-Sterolic Extract of Serenoa Repens (Permixon®) on the Prostate" The Journal of Urology, vol. 164, pp. 876-881.

Feb. 2008—Benway et al., "Bacterial Prostatitis" Urologic Clinics of North America, pp. 23-32.

2008—Chu et al., "Sildenafil and a Compound Stimulating Endothelial NO Syntahse Modify Sexual Incentive Motivation and Copulatory Behaviour in Male Wistar and Fisher 344 Rats" International Society for Sexual Medicine, J Sex Med 2008—pp. 2085-2099.

Apr. 15, 1998—Ferry et al., "A zinc chelator inhibiting gelatinases exerts potent in vitro anti-invasive effects" European Journal of Pharmacology, vol. 351, pp. 225-233.

Oct. 9, 2002—Flegal et al., "Prevalence and Trends in Obesity Among U.S. Adults, 1999-2000" The Journal of the American Medical Association. vol. 288, No. 14, pp. 1723-1727.

2005—Hedlund, et al., "Animal Models of Erectile Dysfunction" Current Protocols in Pharmacology 2005, 5.41.1-5.41.22.

2009—Hogg et al., "The Pathology of Chronic Obstructive Pulmonary Disease" The Annual Review of Pathology: Mechanisms of Disease, vol. 4, pp. 435-459.

May 2008—Kao et al., "Increase of oxidative stress in human sperm with lower motility" American Society for Reproductive Medicine. Fertility and Sterility, vol. 89, No. 5.

Apr. 11, 2003—Ludwig et al., "Chronic prostatitis/ chronic pelvic pain syndrome: seminal markers of inflammation" World Journal of Urology, 2003 vol. 21, pp. 82-85.

Mar. 17, 2004—Ryden et al., "Targets for TNF-alpha-induced lipolysis in human adipocytes" Biochemical and Biophysical Research Communications 318, pp. 168-175.

2000—American Thoracic Society "Idiopathic Pulmonary Fibrosis: Diagnosis and Treatment" Joint Statement of the American Thoracic Society and the European Respiratory Society. Am. J. Respir. Crit. Care Med. vol. 161, pp. 646-664.

\* cited by examiner

A

D

B

E

C

F

A

D

B

E

C

F

A

B

C

BISAMIDE DERIVATIVE OF DICARBOXYLIC ACID AS AN AGENT FOR STIMULATING TISSUE REGENERATION AND RECOVERY OF DIMINISHED TISSUE FUNCTION

CROSS-REFERENCE TO RELATED APPLICATIONS

This application is a continuation of U.S. application Ser. No. 15/576,387, now U.S. Pat. No. 10,076,511, which is a U.S. National Stage application under 35 U.S.C. § 371 of International Application PCT/RU2016/050015 (published as WO 2016/190785), filed May 26, 2016, which claims priority to Application RU 2015120055, filed May 27, 2015. Benefit of the filing date of each of these prior applications is hereby claimed. Each of these prior applications is hereby incorporated by reference in its entirety.

FIELD OF THE INVENTION

The invention relates to the field of medicine, in particular, to pharmacology, urology, andrology, endocrinology, pulmonology, gastroenterology and concerns an agent stimulating tissue regeneration and recovery of diminished functions of tissues and organs.

BACKGROUND OF THE INVENTION

Many pathological conditions, including metabolic syndrome, impaired glucose tolerance, hepatitis, pulmonary emphysema, chronic obstructive pulmonary disease, prostatitis, benign prostatic hyperplasia, hypogonadism, testicular failure, asthenospermia, are accompanied by a decrease in functional activity and structural damage of affected organs.

Metabolic syndrome is a pathological symptom-complex that includes various metabolic and hormonal disorders. Diagnosis "metabolic syndrome" is made in the presence of central obesity and at least two of the following factors: 1) an increase in the triglyceride level ≥150 mg/dl (1.7 mM/l), 2) a reduce in the high-density lipoprotein (HDL) cholesterol level <40 mg/dl (1.03 mM/l) (men), <50 mg/dl (1.29 mM/l) (women), 3) arterial hypertension (arterial pressure (AP)≥130/85 mm Hg or normal AP controlled by hypotensive medications), and 4) an increase in the plasma glucose level ≥100 mg/dl (5.6 mM/l). Today, metabolic syndrome is approximately equally common in men and women; its frequency, for example, in the USA reaches 39% [Flegal K. M., Carroll M. D., Ogden C. L., et al. Prevalence and trends in obesity among US adults, 1999-2000//The Journal of the American Medical Association. 2002. Vol. 288(14). P. 1723-1727].

According to data of different authors, hypogonadism (testosterone deficiency) is revealed in 30-50% of men with obesity and other symptoms of metabolic syndrome (testosterone deficiency). Many researchers have found not only a high prevalence of hypogonadism in men with metabolic syndrome, but also a relationship between the total testosterone plasma level and symptoms of metabolic syndrome. There are reports on both a relationship between overweight and low testosterone levels and a relationship of insulin resistance and a decreased testosterone level in the blood serum of men with obesity [Svartberg J., von Mühlen D., Sundsfjord J., et al. Waist circumference and testosterone levels in community dwelling men. The Tromsø study// European Journal of Epidemiology. 2004. Vol. 19(7). P. 657-667]. A reduction in the serum testosterone level in metabolic syndrome and insulin resistance in men is a result of impaired functional activity of testicular tissue. In accordance with this, the methods of regeneration of testicular tissue, intended for the treatment of hypogonadism both as an independent disease and as a disease associated with metabolic syndrome are of current importance.

An adult pancreas contains approximately $10^9$ cells. Normally worn-out β-cells are constantly replaced by new ones that proliferate in the pancreas (Minami K., Seino S. Current status of regeneration of pancreatic β-cells. Journal of Diabetes investigation. Volume 4, Issue 2. pages 131-141 March 2013). In various pancreatic disorders, such as autoimmune or toxic disorders, β-cells of islets of Langerhans are first characterized by a reduced functional activity, which manifests itself in a decrease in insulin production, and in later stages, they die. Explicit symptoms of pancreatic tissue damage appear when more than 90% of β-cells are destroyed, insulin deficiency becomes permanent, leading to complete dependence on insulin injected from the outside.

Insulin therapy does not allow the accuracy of glycemic regulation that is provided when the islets of Langerhans function normally. There are still attempts to treat damaged pancreas with transplantation of the whole organ, islets of Langerhans, and β-cells. However, transplantation is not always successful (transplant rejection occurs frequently). In successful transplantation, a patient subsequently will continuously need immunosuppressant drugs.

Another problem is impaired glucose tolerance. It is an impaired metabolic response to endogenous or exogenous insulin. This condition leads to an increased insulin plasma concentration compared to the physiological values for the existing glucose concentration. Impaired glucose tolerance in muscle, adipose, and liver tissue is most clinically significant. Impaired tolerance to glucose in the muscle tissue leads to a decrease in the uptake of glucose from the blood into myocytes and its utilization in muscle cells, and in the adipose tissue it manifests itself in resistance to the anti-lipolytic action of insulin, resulting in the accumulation of free fatty acids (FFA) and glycerol. FFAs enter the liver, where they become the main source for the formation of very-low-density atherogenic lipoproteins (VLDAL). Impaired glucose tolerance in the liver tissue is characterized by a decreased synthesis of glycogen and activation of the decomposition of glycogen to glucose (glycogenolysis) and de novo synthesis of glucose from amino acids, lactate, pyruvate, and glycerol (gluconeogenesis). Thus, the treatment of impaired glucose tolerance in tissues makes it possible to restore functional activity of the tissues.

The liver is a vital body gland. It performs about 500 unique functions that support the processes of digestion, inactivation of toxic substances, synthesis of blood coagulation components, metabolism of proteins, amino acids, fats, carbohydrates, nucleic acids, vitamins, trace elements, and the like. The liver tissue is often damaged by chemical, microbial, traumatic, pharmaceutical and other adverse factors. This leads to a decrease in the number of functional hepatocytes. Chronic hepatitis of various etiologies can last for many years, and is often diagnosed in the later stages of the disease, when the likelihood of developing cirrhosis and chronic liver failure increases dramatically [Jung Y1, Witek R P, Syn W K. Signals from dying hepatocytes trigger growth of liver progenitors//Gut. —2010. —Vol. 5. P. 655-65].

The known hepatoprotectors are: Essentiale, lipoic acid, Sirepar, and α-tocopherol. However, these drugs cannot completely protect or restore the impaired functions of membranes, mitochondria and other structures of hepatocytes since any of them has an action only on separate stages of the pathogenesis of hepatitis. In this connection, complex therapy involves the use of hemoprotectors. However, such an approach to the treatment of hepatitis is dangerous because of the interaction of drugs due to polypharmacy and complication of the disease process itself. In addition, almost all drugs of this group have side effects limiting their use. In view of the above, the development of methods that can effectively stimulate liver regeneration remains very actual.

One of the most frequent clinic pathologies of male infertility is an inflammatory disease of the sex accessory glands.

The inflammatory diseases of the sex accessory glands include diseases of the prostate gland associated with inflammation, such as acute bacterial prostatitis, chronic bacterial prostatitis, BPH (benign prostatic hyperplasia), as well as inflammation of the seminal vesicles, such as acute or chronic vesiculitis. Diseases of the prostate gland also include chronic abacterial prostatitis, chronic non-inflammatory prostatitis and category 3B prostatitis [Ludwig M, Vidal A, Diemer Th, Pabst W, Failing K, Weidner W. Chronic prostatitis/chronic pelvic pain syndrome: seminal markers of inflammation.//World J Urol. 2003. Vol. 21, N 2. P. 82-85].

The above pathologies occur in 40-70% of men. Forty percent of men with pathospermia has chronic prostatitis, which in 80% of cases is abacterial (Benway B. M., Moon T. D.//Urol Clin North Am 2008 February; 35(1):23-32).

It should be noted that chronic inflammation of the prostate gland is very often associated with benign prostatic hyperplasia (BPH). BPH-associated hyperprolactinemia leads to erectile insufficiency, oligospermia. This, of course, reduces male reproductive potential [Johri A. M., Heaton J. P., Morales A. Severe erectile dysfunction is a marker for hyperprolactinemia//Int J Import Res. 2001. Vol. 13 No 3. P. 176-82].

Many aspects of prostate disease affect the ejaculate quality since the prostate gland releases the factors supporting, above all, sperm motility. In this regard, correlative testicular failure (secondary infertility) is revealed during the development of prostate disease. Thus, the treatment of prostate gland diseases favorably affects male fertility.

Currently, the drugs that have a positive effect on the factors associated with the course of chronic abacterial prostatitis and BPH include plant extracts—Prostamol Uno [Bayane C. W., Ross M., Donnelly F., Habib F. K.//J. Urol. 2000. Vol. 164, N 3, Pt. 1. P. 876-881]. However, they are not always quite effective.

The inhibition of the formation of androgens (hypogonadism) also results in a reduction in male fertility [Dohie G. R., Diemer A., Giwerman A., Jungwith A., Kora Z., Kraus C. Man Infertility, European Association of Urology 2014. 7].

Male hypogonadism is now found in 4-5 million people. Hypogonadotropic hypogonadism (or secondary hypogonadism) is caused by gonadotropin deficiency. Primary hypogonadism is caused by testicular (testicle) dysfunction. Its non-hereditary forms (acquired hypogonadotropic hypogonadism) may be a result of external actions, administration of drugs (anabolic steroids, metoclopramide, phenotiazid, narcotic drugs, etc.), and radiation therapy [Filicori M. Endocrine basis of reproductive function. —Bologna: Monduzzi Editore, 2000. —R 605; Meczekalski B., Tonetti A., Monteleone R. et al. Hypothalamic amenorrhea with normal body weight: ACTH, allopregnanolone and cortisol responses to corticotrophin—releasing hormone test//Eur. J. Endocrinol. —2000. —V. 142. —R. 280-285].

Patients with secondary hypogonadism are prescribed testosterone [Dohie G. R., Diemer A., Giwerman A., Jungwith A., Kora Z., Kraus C. Man Infertility, European Association of Urology 2014, p. 35]. However, testosterone has many contraindications and side effects.

The known drug Tribestan (manufacturer Sopharma (Bulgaria)) stimulates production of testosterone in men and increases sperm motility, but the effectiveness of this drug is not always high.

Hypogonadism caused by sex gland pathology (hypergonadotropic hypogonadism or testicular failure) refers to the most common form of a reduction in male fertility [Dohie G. R., Diemer A., Giwerman A., Jungwith A., Kora Z., Kraus C. Man Infertility, European Association of Urology 2014, p. 8].

The action of exogenous factors, such as drugs, including cytostatic agents, radiation, temperature increase, is one of the causes of its appearance. Long-term reduction in the spermatogenesis productivity, down to its total arrest, is a consequence of a damage affected type A spermatogonia. Restoration of spermatogenesis after damage is possible only owing to these cells. They do not lose the specificity of the sperm cells because they have irreversibly identified themselves as precursors of spermatogenesis, and, like stem cells, have the colony-formation ability. These cells constitute a deep reserve of the regenerative capacity of spermatogenic tissue.

It is known that the proliferative potential of spermatogenesis can be restored by transplantation of spermatogenic cells. The drug therapy of hypergonadotropic hypogonadism is recommended with testosterone. It stimulates the final phase of spermatomeiosis, i.e. postmitotic division, thereby leading to an increase in the number of spermatocytes and an increase in the spermatogenesis productivity by stimulating its final phase. A disadvantage of this agent is its inefficiency to stimulate spermatogonia, which, as known, are divided mitotically.

In the pharmaceutical market there are no drugs for the treatment of male infertility caused by the depletion of a deep reserve of the regenerative capacity of spermatogenic tissue, and the recovery of the number of committed colony-forming spermatogenic cells. The agent for recovery of male fertility in testicular insufficiency caused by stem cell damage, according to the present invention, has no analogues among the existing therapeutic agents for the treatment of this pathology.

In many cases, a reduction in male fertility is caused by deterioration of sperm quality. The most common ejaculate pathology is asthenospermia (Kao S. H. et. al. Increase of oxidative stress in human sperm with lower motility. Fertil. and Steril. 2008; 89: 5: 1183-1190). Asthenospermia-type failure of spermatogenesis is considered as a separate nosological form. It is a consequence of age-related changes, smoking, inflammation, dyshormonal disorders, and exposure to toxic substances and high temperatures. The treatment of asthenospermia depends on the causes of its appearance. However, these hormonal drugs cause serious side effects and have contraindications.

It is recommended to treat asthenospermia with Speman medication that stimulates spermatogenesis and increases sperm motility. The drug is expensive, consists of a complex composition of medicinal herbs that grow in different countries of the world and have limited raw stock. As a drawback, it should be noted that it is not highly effective.

Pulmonary emphysema, chronic obstructive pulmonary disease (COPD) and idiopathic pulmonary fibrosis (IPF) are severe multifactorial pulmonary disorders characterized by chronic and progressive course in elderly patients (predominantly in men). The clinical pattern and pathogenesis of COPD differs from IPF. The cause of the slightly reversible and progressive airway obstruction in COPD is airway inflammation and emphysematous enlargement of alveoli and bronchioles [Hogg J C, Timens W: The pathology of chronic obstructive pulmonary disease. Annu Rev Pathol 2009, 4:435-459], while the restriction of pulmonary function in IPF is caused by the development of interstitial fibrosis and the formation of "honeycomb" lung [American Thoracic Society: Idiopathic pulmonary fibrosis: diagnosis and treatment. International consensus statement. American Thoracic Society (ATS), and the European Respiratory Society (ERS). Am J Respir Crit Care Med 2000, 161:646-664]. The prevalence of these two lung diseases is completely different. However, every year the incidence and prevalence of IPF is steadily increasing, which is connected, inter alia, with an improvement of diagnostic tools. In turn, the prevalence of COPD has always been very high. The disease is associated to a large extent with inhalation of harmful external substances (mainly due to smoking).

Despite a sufficiently large number of experimental and clinical studies, the understanding of the pathogenesis of pulmonary emphysema and COPD is limited: there are no recognized effective approaches to the treatment of this disease. The existing set of drugs for IPF is limited to glucocorticoids, cyclophosphamide, immunosuppressants, and anticoagulants, is aimed at treating complications, and is essentially a maintenance therapy. Currently, only such a therapeutic agent as Pirfenidone has been approved for the treatment of IPF. Meanwhile, in clinical trials, Pirfenidone did not show an expected high antifibrotic activity at the developed stage of the disease. In addition, the drug has many side effects and requires high doses.

The development of IPF, COPD, malignant neoplasms and many other chronic diseases is associated with a sharp loss of body weight. The greatest danger is the extreme degree of emaciation—cachexia. Clinically, cachexia is manifested by excessive weight loss associated with the ongoing disease process, usually with disproportionate skeletal muscle atrophy.

Diseases leading to cachexia are characterized by a decrease in the functional activity of testicular tissue and, as a consequence, a decrease in the level of testosterone. Testosterone stimulates myoblasts and increases the number of satellite cells, thereby contributing to the protein synthesis and recovery of damaged muscles [Bhasin S., Taylor W. E., Singh R. et al. The mechanisms of androgen effects on body composition: mesenchymal pluripotent cell as the target of androgen action. J Gerontol Med Sci 2003; 58A: M1103-1110]. Testosterone also suppresses the synthesis of proinflammatory cytokines IL-1, IL-6, TNFα and stimulates the production of anti-inflammatory cytokine IL-10. An extreme degree of emaciation in various diseases is associated with an inflammation. Inflammatory mediators prevent the synthesis of muscle proteins in cachexia, and are involved in lipolysis and beta-oxidation of fatty acids [Ryden M., Arvidsson E., Blomqvist L., Perbeck L., Dicker A., Arner P. Targets for TNF-alpha-induced lipolysis in human adipocytes. Biochem Biophys Res Commun 2004; 318:168-175].

Unfortunately, there is still no single recognized approach to the treatment of cachexia. Numerous attempts have been made to correct this condition. Therapy of patients with severe weight loss includes medications of testosterone, growth hormones (somatropin), appetite stimulants (serotonin antagonists, progestogens, dronabinol), and inhibitors of gluconeogenesis (hydrazine sulfate), but their effectiveness is not sufficient.

SUMMARY

Aspects of the invention relate to a method for stimulating tissue regeneration and recovery of diminished functions of tissues and organs, and more particularly, regeneration and recovery of diminished functions of pancreatic tissue, liver tissue, lung tissue, muscular tissue, spermatogenic tissue, testicular tissue, and prostate tissue.

Further aspects of the invention relate to an agent normalizing a reduced male fertility (treatment of male sterility) that can be caused by such pathological conditions as hypogonadism, in particular hypogonadotropic or hypergonadotropic hypogonadism, asthenospermia, erectile dysfunction, correlative testicular failure, testicular failure, and other disorders.

The present invention can be used for the treatment and prevention of pathological conditions selected from the group including metabolic syndrome, impaired glucose tolerance, hepatitis, particularly chronic hepatitis, idiopathic pulmonary fibrosis, pulmonary emphysema, chronic obstructive pulmonary disease, cachexia, hypogonadism, preferably hypogonadotropic hypogonadism or hypergonadotropic hypogonadism, prostatitis, benign prostatic hyperplasia, correlative testicular failure and autoimmune orchitis.

The invention also relates to an agent for recovery of sperm motility.

In certain embodiments, the present invention provides an agent for regeneration and recovery of diminished functions of tissues. Such an agent will, in particular, promote the treatment of glucose tolerance disorders, hepatitis, pulmonary emphysema, chronic obstructive pulmonary disease, idiopathic pulmonary fibrosis, cachexia, and will promote the recovery of male reproductive function, and will overcome the drawbacks of the known agents described above.

More specifically, the present invention may provide an agent that promotes regeneration of tissues, in particular pancreatic, liver, lung, testicular, prostate, and muscle tissues. In particular, the agent according to the invention should promote the regeneration of testicular tissue and prostate tissue.

The present invention may further provide an agent for lowering the blood glucose level increased, in particular, due to pathological conditions such as metabolic syndrome or impaired glucose tolerance.

The present invention may yet further provide an agent for recovery of liver function reduced in particular due to pathological conditions, such as viral chronic hepatitis.

The present invention may yet further provide an agent for normalizing a reduced male sexual activity caused, in particular, by such pathologies as hypogonadism, correlative testicular failure, and testicular failure.

The present invention may yet further provide an agent for recovery of spermatogenesis (including sperm motility) reduced, in particular, due to such pathologies as metabolic syndrome, prostatitis, hypogonadism, asthenospermia, testicular failure, and other diseases.

The present invention may yet further provide an agent for recovery of a disturbed histoarchitectonics and functions of pulmonary tissue, which is caused, in particular, by such pathologies as emphysema, idiopathic lung fibrosis and chronic obstructive pulmonary disease.

The present invention may yet further provide an agent for recovery of liver structure and function.

The present invention may yet further provide an agent for recovery of pancreas structure and function affected by such diseases as metabolic syndrome and impaired glucose tolerance.

A Treamid-based drug may provide an agent for the treatment and/or prevention of the above pathological conditions. Said agent is a bisamide derivative of dicarboxylic acid of formula (I):

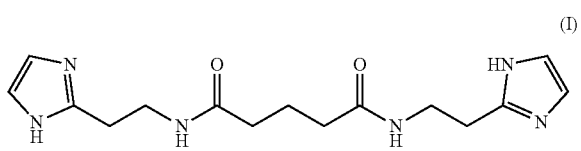 [SMILES: O=C(CCCC(=O)NCCc1ncc[nH]1)NCCc1ncc[nH]1]

(I)

or a pharmaceutically acceptable salt thereof.

This compound is described in RU301116822 (published on Oct. 20, 2014) relating to novel compounds suitable for use as metal chelators, including for the treatment of diseases associated with metal chelating activity.

The inventor has discovered, at first, that Treamid is able to efficiently regenerate tissues and restore their diminished functions; this, in particular, concerns the male reproductive system tissues. Treamid reduces the severity of morphological changes in the prostate gland in abacterial prostatitis and BPH, restores sperm motility, enhances sex drive and copulatory activity, which, in combination, leads to the recovery of male reproductive function.

A: Treamid at a dose of 10 mg/kg (×100); B: Intact control (×100); C: Pathological control (×100); D: Treamid at a dose of 10 mg/kg (×400); E: Intact control (×100); F: Intact control (×400)

Figure 2:
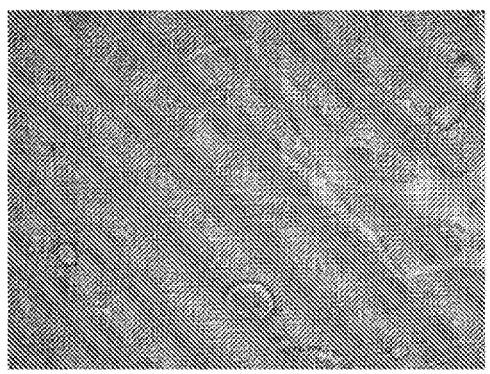
Figure 2:
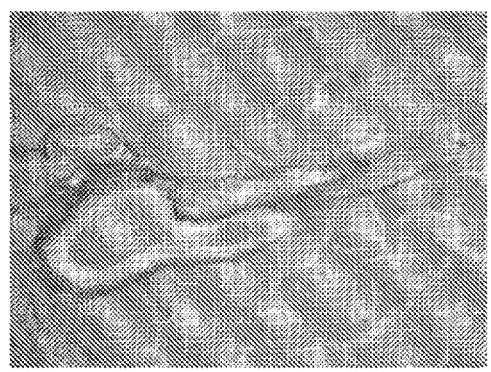
Figure 2:
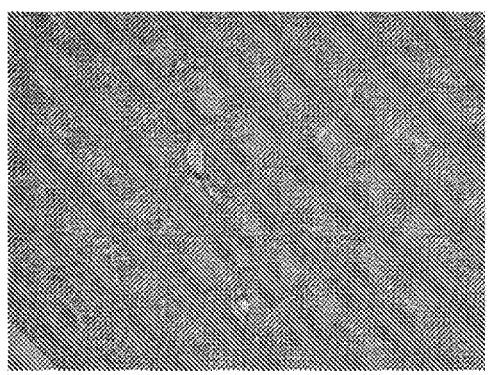
Figure 2:
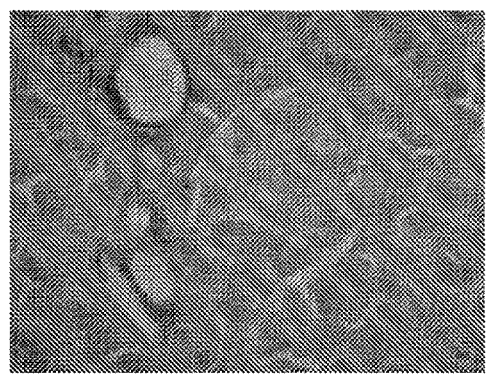
Figure 2:
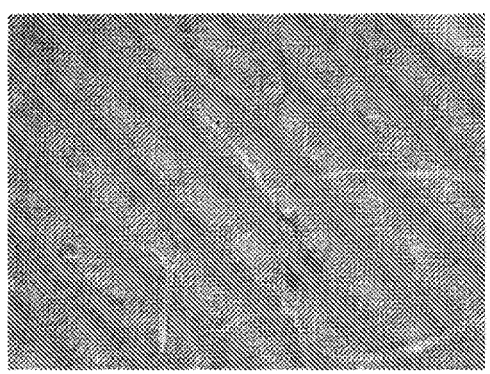
Figure 2:
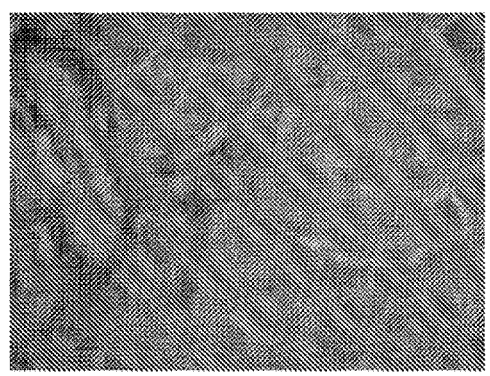

FIG. 2 is a morphological pattern of pancreas in male C57Bl/6 mice of intact control, on Day 70 of untreated metabolic disorders (pathological control) and on Day 70 of metabolic disorders treated with the Treamid at a dose of 10 mg/kg. Staining with picrofuxin by Van Gieson.

A: Treamid at a dose of 10 mg/kg (×100); B: Intact control (×100); C: Pathological control (×100); D: Treamid at a dose of mg/kg (×400); E: Intact control (×400); F: Pathological control (×400)

Figure 3:
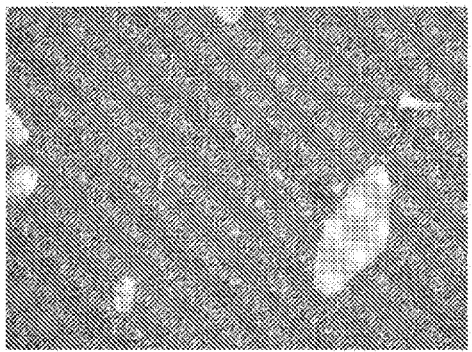
Figure 3:
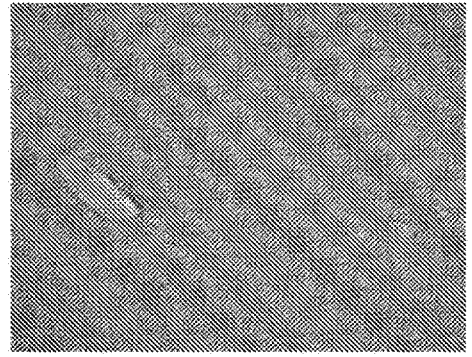
Figure 3:
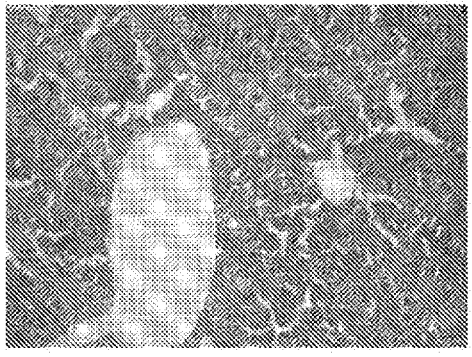
Figure 3:
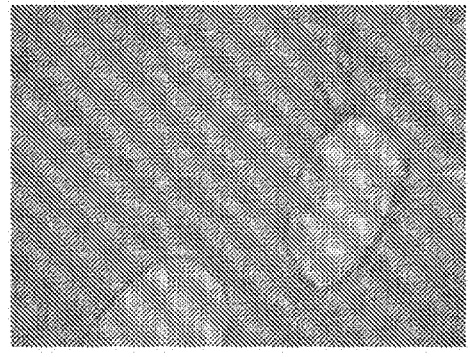
Figure 3:
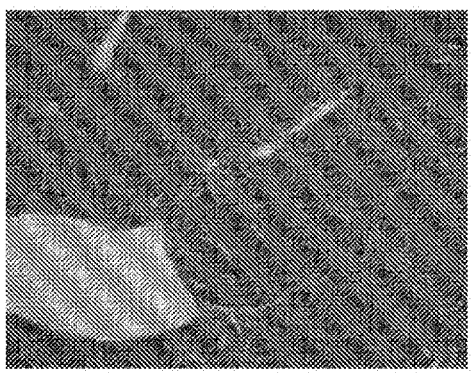
Figure 3:
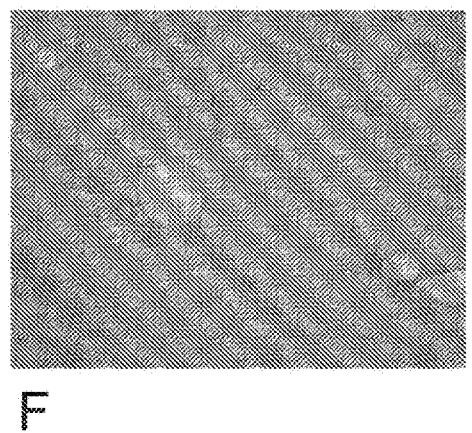

FIG. 3 is a morphological pattern of liver in male C57Bl/6 mice of an intact control group, a group of pathological control of chronic toxic hepatitis, and a group treated with Treamid at a dose of 10 mg/kg; magnification is 100×; the preparations were prepared on Day 28 of the study.

A, B, and C are the staining with hematoxylin and eosin; D, E, and F are the staining with picrofuxin by Van Gieson. A and D are intact control; B and E are pathological control; C and F are animals with hepatitis treated with Treamid at a dose of 10 mg/kg.

Figure 4:
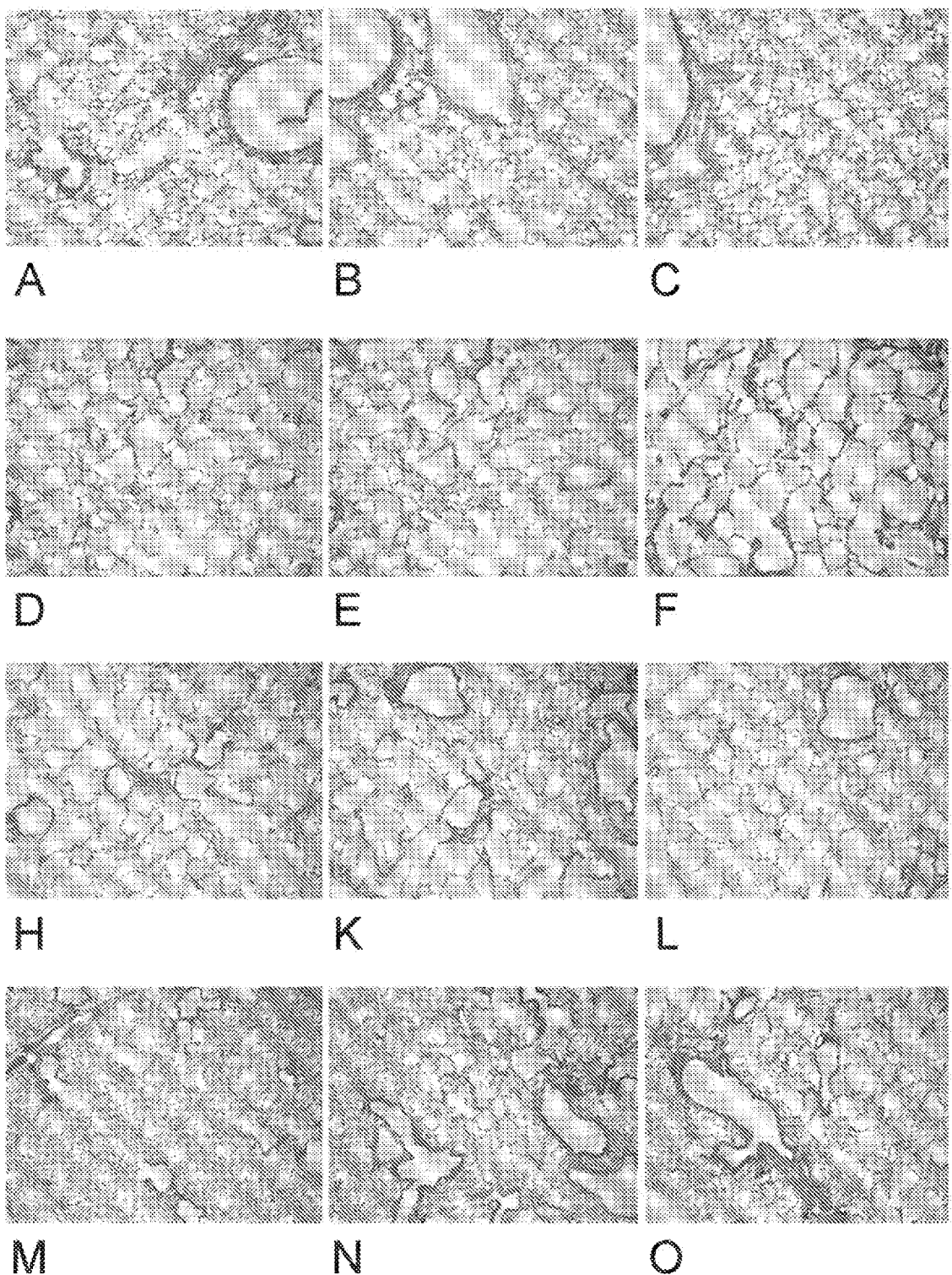

FIG. 4 is a morphological pattern of lungs in male C57Bl/6 mice of an intact control group, a pathological control group of mice with emphysema on Days 14 and 30, and a group of animals treated with Treamid at a dose of 10 mg/kg, on Day 30. Magnification is 100×. It is the staining with hematoxylin and eosin Intact control: A—lung apex; B—middle lung field, and C—lower lung field. Pathological control (Day 14): D—lung apex; E—middle lung field, and F—lower lung field. Pathological control (Day 30): H—lung apex; K—middle lung field, and L—lower lung field. The group of animals treated with Treamid: M—lung apex; N—middle lung field, and O—lower lung field.

Figure 5:
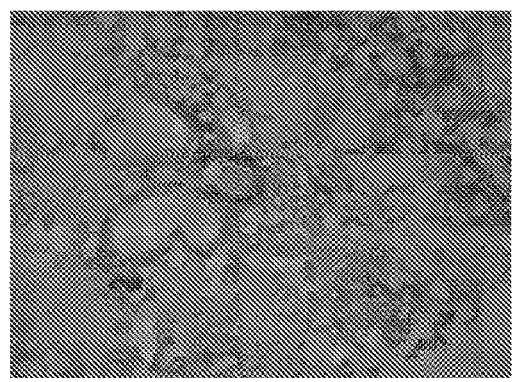
Figure 5:
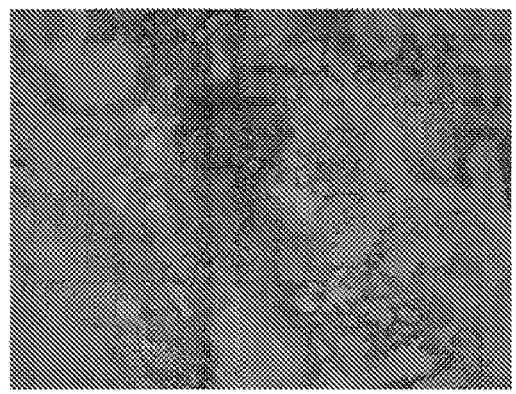
Figure 5:
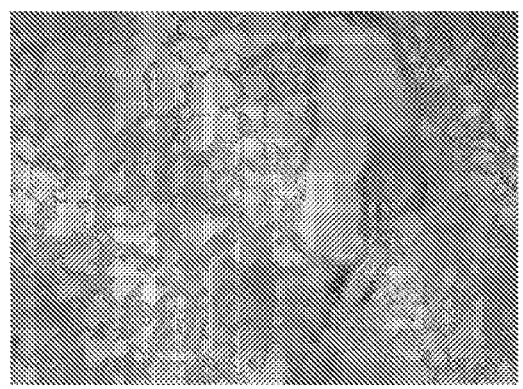

FIG. 5 is a morphological pattern of lungs in male C57Bl/6 mice of intact control (A), pathological control (B), and a group of mice with pulmonary fibrosis treated with Treamid at a dose of 10 mg/kg (C). It is the staining with picrofuxin by Van Gieson (magnification of 100×); the preparations were prepared on Day 21 of the experiment.

DETAILED DESCRIPTION OF EMBODIMENTS

The present invention relates to a pharmaceutical composition for regeneration of tissues, comprising an effective amount of a compound of formula (I):

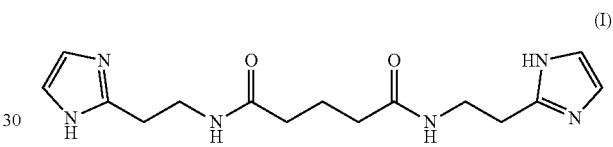

(I)

or a pharmaceutically acceptable salt thereof and a pharmaceutically acceptable carrier. The present invention also relates to a medicament for regeneration of tissues, which is a compound of formula (I) or a pharmaceutically acceptable salt thereof.

In one embodiment of the invention, the tissue is selected from the group comprising a pancreatic tissue, a liver tissue, a lung tissue, a muscular tissue, a spermatogenic tissue, a testicular tissue, and a prostate tissue.

The present invention also relates to a method for regenerating a tissue, comprising administering to a patient in need thereof an effective amount of a compound of formula (I) or a pharmaceutically acceptable salt thereof. Further, the present invention relates to use of a compound of formula (I) or a pharmaceutically acceptable salt thereof, for regeneration of tissues. In one embodiment of the invention, the tissue is selected from the group comprising a pancreatic tissue, a liver tissue, a lung tissue, a muscular tissue, a spermatogenic tissue, a testicular tissue, and a prostate tissue. The present invention also relates to use of a compound of formula (I) or a pharmaceutically acceptable salt thereof for the treatment of pathological conditions associated with a structural damage of tissues. In one embodiment of the invention, the pathological condition is selected from the group including metabolic syndrome, impaired glucose tolerance, hepatitis, in particular chronic hepatitis and toxic hepatitis, idiopathic pulmonary fibrosis (IPF), pulmonary emphysema, chronic obstructive pulmonary disease (COPD), and cachexia, in particular, caused by impaired glucose tolerance, idiopathic pulmonary fibrosis, chronic obstructive pulmonary disease, cancer and other diseases. In another embodiment of the invention, the disease is hypogonadism and associated erectile dysfunction and/or impaired libido, prostatitis and associated erectile dysfunction and/or impaired libido, benign prostatic hyperplasia, correlative testis failure, or autoimmune orchitis, wherein the hypogonadism preferably is hypogonadotropic hypogonadism or hypergonadotropic hypogonadism. Prostatitis may be abacterial prostatitis, autoimmune prostatitis, or category 3B prostatitis.

In addition, the present invention relates to a pharmaceutical composition for normalizing a reduced male fertility, comprising an effective amount of a compound of formula (I) or a pharmaceutically acceptable salt thereof and a pharmaceutically acceptable carrier.

The present invention also relates to a medicament for normalization of a reduced male fertility, wherein the medicament is a compound of formula (I) or a pharmaceutically acceptable salt thereof.

The present invention also relates to a method for normalizing a reduced male fertility, comprising administering to a patient in need thereof an effective amount of a compound of formula (I) or a pharmaceutically acceptable salt thereof. Further, the present invention relates to use of a compound of formula (I) or a pharmaceutically acceptable salt thereof, for normalization of a reduced male fertility. In a preferable embodiment, the reduced male fertility is caused by a pathological condition including hypogonadism, preferably hypogonadotropic hypogonadism or hypergonadotropic hypogonadism, asthenospermia, erectile dysfunction, testicular failure, and other diseases. The reduced male fertility also may be caused by a suppressed copulatory activity and libido, which, in particular, may be provoked by the above-mentioned diseases.

In addition, the present invention relates to a pharmaceutical composition for recovery of sperm motility, comprising an effective amount of a compound of formula (I) or a pharmaceutically acceptable salt thereof and a pharmaceutically acceptable carrier. The present invention also relates to a medicament for recovery of sperm motility, wherein the medicament is a compound of formula (I) or a pharmaceutically acceptable salt thereof. The invention further relates to a method for recovery of sperm motility, comprising administering to a patient in need thereof an effective amount of a compound of formula (I) or a pharmaceutically acceptable salt thereof. The present invention also relates to use of a compound of formula (I) or a pharmaceutically acceptable salt thereof for recovery of sperm motility, wherein said reduction may be caused by hypogonadism, asthenospermia, correlative testicular failure, and testicular failure. The reduction in motility also may be caused by suppression of copulatory activity and libido of various etiologies.

The present invention also relates to a pharmaceutical composition for reducing a blood glucose level in the treatment and/or prevention of a pathological condition, comprising an effective amount of a compound of formula (I). The present invention also relates to a medicament for reducing a blood glucose level, wherein the medicament is a compound of formula (I). Further, the present invention relates to a method for reducing a blood glucose level in the treatment and/or prevention of a pathological condition, comprising administering to a subject in need thereof a therapeutically effective amount of a compound of formula (I) or a pharmaceutically acceptable salt thereof. The pathological condition may be selected from the group including metabolic syndrome and impaired glucose tolerance. The invention also relates to use of a compound of formula (I) or a pharmaceutically acceptable salt thereof for reducing a blood glucose level.

Furthermore, the invention relates to a pharmaceutical composition for recovery of liver structure and function in the treatment and/or prevention of a pathological condition, comprising an effective amount of a compound of formula (I) or a pharmaceutically acceptable salt thereof, and a pharmaceutically acceptable carrier.

The present invention also relates to a medicament for recovery of liver structure and function, wherein the medicament is a compound of formula (I). The pathological condition may be selected from the group including hepatitis, in particular chronic hepatitis and toxic hepatitis. The present invention also relates to use of a compound of formula (I) or a pharmaceutically acceptable salt thereof for recovery of liver structure and function.

In addition, the invention relates to a pharmaceutical composition for recovery of lung structure and function in the treatment and/or prevention of a pathological condition, comprising an effective amount of a compound of formula (I) or a pharmaceutically acceptable salt thereof and a pharmaceutically acceptable carrier. The pathological condition is selected from the group including chronic obstructive pulmonary disease (COPD), pulmonary emphysema, and idiopathic pulmonary fibrosis. The present invention also relates to a medicament for recovery of lung structure and function, wherein the medicament is a compound of formula (I). Further, the present invention relates to use of a compound of formula (I) or a pharmaceutically acceptable salt thereof for recovery of lung structure and function.

In addition, the invention relates to a pharmaceutical composition for recovery of pancreas structure and function in the treatment and/or prevention of a pathological condition, comprising an effective amount of a compound of formula (I) or a pharmaceutically acceptable salt thereof and a pharmaceutically acceptable carrier. The pathological condition may be selected from the group including metabolic syndrome and impaired glucose tolerance.

The present invention also relates to a medicament for recovery of pancreas structure and function, wherein the medicament is a compound of formula (I). In addition, the invention relates to use of a compound of formula (I) or a pharmaceutically acceptable salt thereof for recovery of pancreas structure and function.

The invention relates to an agent for stimulation of tissue regeneration and recovery of diminished functions of tissues and organs; more particularly, to the regeneration and recovery of diminished functions of pancreatic tissue, a liver tissue, a lung tissue, a muscular tissue, a spermatogenic tissue, a testicular tissue, and a prostate tissue.

An object of the invention is an agent promoting regeneration of tissues, in particular the tissues involved in the activity of male sex glands. This agent is a bisamide derivative of dicarboxylic acid of formula (I):

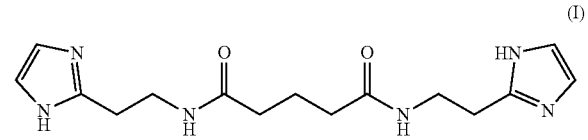 [SMILES: O=C(CCCC(=O)NCCc1ncc[nH]1)NCCc1ncc[nH]1]

or a pharmaceutically acceptable salt thereof, also known as Treamid.

Pharmaceutically acceptable salts of a compound of formula (I) according to the present invention include organic acid addition salts (for example formate, acetate, maleate, tartrate, methanesulfonate, benzenesulfonate, toluenesulfonate, etc.), inorganic acid addition salts (for example hydrochloride, hydrobromide, sulfate, phosphate, etc.), salts with amino acids (for example, salts of an aspartic acid, glutamic acid, etc.), preferably hydrochlorides and acetates.

The inventor has discovered, at first, that Treamid has an ability to efficiently regenerate tissues and restore diminished functions of tissues, in particular, of the tissues involved in the activity of male sex glands.

The tissues involved in the activity of male sex glands include various epithelial tissues, in particular the epithelium of convoluted seminiferous tubules (testicular tissue), the epithelium (of acini) of the prostate structural units (prostate tissue), and various connective tissues.

The inventor also has found that Treamid effectively normalizes a reduced male sexual activity caused by, in particular, such pathologies as hypogonadism, correlative testicular failure, and testicular failure.

In addition, the inventor has found that Treamid effectively recovers sperm motility caused by in particular such pathologies as hypogonadism, asthenospermia, correlative testicular failure, and testicular failure.

A compound of formula (I) is administered in an effective amount that provides a desired therapeutic effect.

A compound of formula (I) can be administered orally, topically, parenterally, intranasally, by inhalation and rectally in unit dosage forms containing non-toxic pharmaceutically acceptable carriers. The term "parenteral administration", as used herein, means subcutaneous, intravenous, intramuscular or intrathoracic injections or infusions.

A compound of formula (I) according to the present invention may be administered to a patient at daily doses of from 0.1 to 100 mg/kg of human body weight, preferably at doses of from 0.01 to 25 mg/kg, one or more times a day.

It should be noted that a particular dose for a particular patient will depend on many factors, including the activity of the used compound, patient's age, body weight, gender, general health condition, and dietary regimen; time and route of drug administration, its excretion rate from the body; particularly used combination of drugs, and disease severity in an individual to be treated.

Pharmaceutical compositions according to the present invention comprise a compound of formula (I) in an amount effective for achieving a desired result, and may be administered in unit dosage forms (for example, in solid, semisolid, or liquid forms) that comprise compounds according to the present invention as an active agent in a mixture with a carrier or an excipient suitable for intramuscular, intravenous, oral, sublingual administration, administration by inhalation, intranasal, and intrarectal administration. The active agent may be included into a composition together with commonly used nontoxic pharmaceutically acceptable carriers suitable for producing solutions, tablets, pills, capsules, coated pills, suppositories, emulsions, suspensions, ointments, gels, patches, and any other dosage forms.

Various compounds may be used as excipients, such as saccharides, for example, glucose, lactose, of sucrose; mannitol or sorbitol; cellulose derivatives; and/or calcium phosphates, for example, tricalcium phosphate or calcium hydrophosphate. Compounds suitable as a binder include starch paste (for example, corn, wheat, rice, or potato starch), gelatin, tragacanth, methylcellulose, hydroxypropyl methylcellulose, sodium carboxymethylcellulose, and/or polyvinylpyrrolidone. If necessary, disintegrating agents may be used, such as the above-mentioned starches and carboxymethylstarch, cross-linked polyvinylpyrrolidone, agar, or alginic acid or a salt thereof, such as sodium alginate. Optionally used additives include flowability control agents and lubricants, such as silica, talc, stearic acid and salts thereof, such as magnesium stearate or calcium stearate, and/or propylene glycol. The core of a coated pill is usually coated with a layer that is stable to the action of the gastric acid. For this purpose, it is possible to use concentrated solutions of saccharides that can optionally contain gum arabic, talc, polyvinylpyrrolidone, polyethylene glycol and/or titanium dioxide, and suitable organic solvents or mixtures thereof.

Stabilizing agents, thickening agents, colorants, and flavorants also may be used as additives.

As an ointment base it is possible to use hydrocarbon ointment bases, such as white petrolatum and yellow petrolatum (*Vaselinum album* and *Vaselinum flavum*, respectively), petrolatum oil (*Oleum Vaselini*), and white and liquid ointment (*Unguentum album* and *Unguentum flavum*), and solid paraffin and wax are useful as consistency-increasing additives; absorptive ointment bases, such as hydrophilic petrolatum (*Vaselinum hydrophylicum*), lanoline (*Lanolinum*), and cold cream (*Unguentum leniens*); water-removable ointment bases, such as hydrophilic ointment (*Unguentum hydrophylum*); and water-soluble ointment bases, such as polyethylene glycol ointment (*Unguentum Glycolis Polyaethyleni*); bentonite bases; and others.

Methylcellulose, carboxymethylcellulose sodium salt, oxypropylcellulose, polyethylene glycol or polyethylene oxide, and carbopol may be used as a base for gels.

A base for suppositories may be a water-insoluble base, such as cocoa butter; a water-soluble or water-miscible base, such as gelatin-glycerol or polyethylene oxide base; and a combined soap-glycerol base.

In preparing a unit dosage form, the amount of the active agent used in combination with a carrier may vary depending on a recipient to be treated, and a particular route of administration of the therapeutic agent.

For example, when a compound according to the present invention is used in the form of a solution for injections, the amount of the active agent in this solution is up to 5 wt. %. A diluent used may be a 0.9% sodium chloride solution, distilled water, Novocaine solution for injections, Ringer solution, glucose solution, and specific solubilizing adjuvants.

When compounds according to the present invention are administered in the form of tablets or suppositories, their amount is up to 200 mg per unit dosage form.

Dosage forms according to the present invention are produced by standard methods, such as blending, granulation, forming coated pills, dissolution, and lyophilization.

Further, the effectiveness of Treamid is demonstrated in the presented experimental examples that are intended to illustrate embodiments of the invention, but not to limit its scope.

All the data obtained in the experimental studies were statistically processed using the nonparametric Mann-Whitney U-test. In studies, a significance level of 0.05 was considered statistically valid.

Example 1

Study of the Effectiveness of Treamid for Recovery of Sperm Motility in Asthenospermia Asthenospermia was simulated by using Etoposide exhibiting pronounced prooxidant properties. The use of the drug that induces an increase in the free radical level was due to the fact that according to modern ideas, the direct cause of asthenospermia is oxidative stress (Kao S. H. et. al. Increase of oxidative stress in human sperm with lower motility. Fertil. and Steril. 2008; 89: 5: 1183-1190).

Treamid was administered at a dose of 5 mg/kg in the treatment course (for 10 days after administration of Etoposide) and in the course of preventive therapy (for 5 days before and 5 days after administration of Etoposide) to male rats that had a reduced motility of mature sperm.

The experiments were performed on 50 male Wistar rats (3 months of age). Etoposide was administered once intravenously at the maximum tolerated dose of 30 mg/kg.

The effectiveness of Treamid was assessed by the percentage of motile sperm forms isolated from the epididymis.

In the first series, the results of the studies were compared with those obtained for administration of the reference drug, Speman, that was administered intragastrically at a dose of 140 mg/kg.

The results of the studies are presented in Tables 1-2.

TABLE 1

The number of motile sperm cells (in %) in animals receiving Treamid for 5 days before and for 5 days after (course of preventive therapy) administration of Etoposide

| No | Background | Control | Treamid, 5.0 mg/kg | Speman |
|---|---|---|---|---|
| 1 | 87.37 | 75.58 | 74.67 | 78.04 |
| 2 | 94.74 | 66.54 | 85.26 | 74.67 |
| 3 | 96.84 | 70.11 | 77.42 | 78.15 |
| 4 | 83.12 | 63.06 | 79.09 | 66.67 |
| 5 | 91.35 | 58.95 | 82.72 | 70.18 |
| X ± m | 90.68 ± 2.48 | 66.85 ± 2.86 # | 79.83 ± 1.88 #* ◊ | 73.54 ± 2.25 #* |

Notes:
here and below:
- differences are significant vs. background;
*differences are significant vs. control;
◊ differences are significant vs. reference drug

TABLE 2

| Male No. | Group name | | |
|---|---|---|---|
| | Background | Control | Treamid, 5.0 mg/kg for 10 days after administration of Etoposide |
| 1 | 78.10 | 60.26 | 65.52 |
| 2 | 74.42 | 53.79 | 75.34 |
| 3 | 75.90 | 57.58 | 74.55 |
| 4 | 73.63 | 52.98 | 69.44 |
| 5 | 79.66 | 54.38 | 70.20 |
| M ± m | 76.34 ± 1.13 | 55.80 ± 1.36 # | 71.01 ± 1.80* |

The presented experimental data showed that on Days 5 and 10 after administration of Etoposide (control), the percentage of motile sperm cells significantly decreased and was 73-74% of background values. In each of the series of the experiments, the percentage of motile sperm cells, in case of administration of Treamid, significantly increased compared to the control (Etoposide), and in the first series, compared to Speman drug. In the second series of the experiments, the percentage of motile sperm cells in the experimental groups did not differ from that in intact animals (background). The obtained data suggest that Treamid is an effective agent for recovery of sperm motility.

Example 2

Study of the Effectiveness of Treamid for Recovery of Sperm Motility in Hypogonadotropic Hypogonadism Hypogonadotropic hypogonadism was simulated by the administration of Synestrol. Estrogens are able to inhibit the secretion of LH (Luteinizing hormone) and FSH (follicle stimulating hormone). An increase in the concentration of estrogens in a male body is accompanied by an increase in the content of sex-steroid-binding globulins, which leads to a decrease in the concentration of free testosterone and to the appearance of asthenospermia.

Experiments were performed on 36 male Wistar rats (3 months of age). For 30 days after the beginning of the experiment, all male rats (except for the background group) were intramuscularly injected with Synestrol at a dose of 50 U/kg/day. Further, from Day 31 to Day 45 of the experiment, the animals of the experimental group, in addition to Synestrol, were intraperitoneally administered Treamid at dose of 0.5 mg/kg or reference drug Tribestan at a dose of 70 mg/kg. The effectiveness of Treamid was estimated by the number of motile sperm forms (percentage of motile sperm forms) isolated from the epididymis. The results of the studies were compared with those for the administration of Synestrol (control) and reference drug Tribestan.

The results of the studies are presented Table 3.

TABLE 3

The number of motile sperm cells (%)

| No | Background | Control | Treamid | Tribestan |
|---|---|---|---|---|
| 1 | 85.43 | 0.00 | 72.63 | 0.00 |
| 2 | 83.69 | 53.06 | 66.67 | 0.00 |
| 3 | 85.26 | 55.97 | 66.99 | 60.21 |
| 4 | 74.72 | 58.87 | 85.55 | 50.00 |
| 5 | 77.66 | 21.43 | 68.08 | 57.53 |
| 6 | 87.64 | 65.91 | 67.04 | 0.00 |
| 7 | 80.22 | 47.22 | 56.84 | 44.93 |
| 8 | 80.89 | 50.00 | 78.65 | 67.04 |
| 9 | 75.26 | 64.93 | 59.09 | 9.09 |
| X ± m | 81.20 ± 1.55 | 46.38 ± 7.27# | 69.06 ± 2.98#* ◊ | 32.09 ± 9.69# |

Note:
differences are significant vs. background;
*differences are significant vs. control;
◊ differences are significant vs. reference drug The presented experimental data show that the percentage of motile sperm forms in intact rats was 81.20±1.55, which corresponds to the species norm. The administration of Synestrol to the animals (control group) led to a significant decrease in the number of motile sperm forms to 46.38±7.27%, which was 57% of the background. In the group of experimental animals, this index statistically significantly exceeded the control values by 49%. Tribestan did not have an effect.

Thus, in hypogonadotropic hypogonadism, Treamid effectively recovers the sperm motility.

Example 3

Study of the Effectiveness of Treamid for Recovery of Copulatory Activity

Reduction of copulatory activity caused by androgen deficiency was simulated by administration of Synestrol to male rats.

The model is based on the antagonism of androgenic and estrogenic hormones. The administration of Synestrol to male rats leads to the suppression of the sexual activity in animals.

Experiments were performed on 36 male Wistar rats (3 months of age). For 30 days after the beginning of the experiment, all male rats (except for the intact group (background)) were intramuscularly injected with Synestrol at a dose of 50 U/kg/day. Further, from Day 31 to Day 45 of the experiment, animals of the experimental groups, in addition to Synestrol, were intraperitoneally administered Treamid at a dose of 1.5 mg/kg and reference preparation Tribestan at a dose of 70 mg/kg. The sexual activity was estimated by the pair-test of sexual behavior. For this purpose, female rats in the estrus stage caused by a preliminary 4-fold injection of Synestrol were involved in the experiment. The effectiveness of Treamid was estimated by the following indices: latency until the first mating attempt (LFM), the number of mating attempts (mounts), and the number of ejaculations. The obtained data were compared with those of the same animals before the experiment (the first test) and with the data in the control group (the second test).

The results of the studies are presented Table 4.

Experiments on studying the effect of Treamid on copulatory activity were carried out on 76 Wistar rats (14 months and 19 months of age). Treamid was administered intragastrically for 14 days at a dose of 5 mg/kg. Reference drug Sildenafil (100 mg, PFIZER PGM, France) was also administered intragastrically, which corresponded to clinical use, at a dose of 3 mg/kg twice a week. The sexual activity was estimated by the pair-test of sexual behavior. For this purpose female rats in the estrus stage caused by a preliminary 4-fold injection of the Synestrel were involved in the experiment. The effectiveness of Treamid was estimated by the following indices: latency until the first mating attempt (LFM), the number of mating attempts (MN), and the number of ejaculations (EN). The obtained data were compared with those of the same animals before the administration of Treamid (the first test) and with the data in the control group (the second test).

Experiments on studying the effect of Treamid on sexual motivation were carried out on 40 male Wistar rats (14 months of age). A model for a targeted search for novel

TABLE 4

The effect of Treamid on the indices of sexual behavior of male rats treated with Synestrol

| | First test | | | Second test | | |
|---|---|---|---|---|---|---|
| No | LFM, sec | The number of mounts, abs. | Ejaculating animals, % | LFM, sec | The number of mounts, abs. | Ejaculating animals, % |
| Background | 145.89 ± 84.42 | 4.56 ± 0.71 | 22.22% | 84.67 ± 34.91 | 9.22 ± 1.19 | 44.44 |
| Control | 387.78 ± 122.24# | 7.11 ± 2.86 | 0.00%# | 234.44 ± 55.69# | 5.00 ± 1.46# | 0.00# |
| Treamid 1.5 | 373.89 ± 112.89# | 5.89 ± 1.91 | 0.00%# | 381.22 ± 115.18# | 8.00 ± 3.12 | ◊ 44.44* |
| Tribestan | 425.67 ± 123.67# | 5.00 ± 1.56 | 0.00%# | 381.89 ± 123.85# | 5.00 ± 1.41# | ◊ 22.22* |

Note:
differences are significant vs. background at $P \leq 005$, comparison in one test;
*differences are significant vs. control at $P \leq 005$, comparison in one test;
◊ - differences are significant at $P \leq 005$ within the group in comparison of the first and second tests.

The presented experimental data showed that male rats receiving only Synestrol were characterized by the absence of ejaculations and an increased LFA. In the animals treated with Treamid, ejaculations were registered in 44% of cases (as well as in intact animals). Their number exceeded the control values and the values of the same animals in the first test. In addition, the number of mating attempts in the experimental group was restored to the control level. The effectiveness of reference drug Tribestan was less pronounced. Thus, Treamid effectively restores copulatory activity in animals with androgen deficiency.

Example 4

Study of the Effectiveness of Treamid for Recovery of Copulatory Function and Sexual Motivation, Reduced Due to Age-Related Changes, in Male Rats Erectile dysfunction was simulated by using animals of late and senile reproductive age (14-19 months). Suppression of sexual motivation was simulated by using animals of late reproductive age (14 months).

agents for the therapy of this pathology was used as an experimental model of sexual incentive motivation in rats [Xi Chu, Ekaterina S. Zhavbert, Julia L. Dugina, Irina A. Kheyfets, Svetlana A. Sergeeva, Oleg I. Epstein, Anders Agmo Sindenafil and a compound stimulating endothelial NO synthase modity sexual incentive motivation and copulatory behavior in male wistar and fisher 344//J Sex Med. —2008. —5. —P. 2085-2009]. This model is based on the fact that rats are social animals and seek not only sexual, but also social contacts. The assessment of sexual motivation involves determining the time spent near a sexual stimulus and the score of preference in animals without direct contact with "social" and "sexual" stimuli. The sexual stimulus was a female rat in estrus stage, and the social stimulus was a male rat.

The results of studies of the effect of Treamid on copulatory behavior and sexual motivation, carried out on animals of late reproductive and senile age are presented in Tables 5, 6, 7 and 8.

TABLE 5

Indices of copulatory behavior of male rats of late reproductive age (14 months)

| Age of animals (months) | Group | First test, before administration of drugs | | |
|---|---|---|---|---|
| | | LFM | MN | EN |
| 3 | Background | 166.00 ± 26.41 | 7.25 ± 1.22 | 0.25 ± 0.16 |
| 14 | Control | 592.83 ± 87.68 # | 1.50 ± 0.53 # | 0.00 ± 0.00 # |
| | Treamid (5 mg/kg) | 559.08 ± 93.55 # | 1.42 ± 0.50 # | 0.00 ± 0.00 # |
| | Sildenafil (3 mg/kg) | 610.08 ± 88.34 # | 1.58 ± 0.56 # | 0.00 ± 0.00 # |

TABLE 6

Indices of copulatory behavior of male rats of late reproductive age (14 months) after administration of Treamid

| Age of animals (months) | Group | Second test, after 14-day administration course | | |
|---|---|---|---|---|
| | | LFM | MN | EN |
| 3 | Background | 155.88 ± 32.66 | 11.25 ± 1.88 | 0.25 ± 0.16 |
| 14 | Control | 455.91 ± 92.22 # | 3.36 ± 0.75 # | 0.00 ± 0.00 # |
| | Treamid (5 mg/kg) | 364.80 ± 127.66 | 6.90 ± 1.88 ◊ | 0.60 ± 0.22 ◊ * |
| | Sildenafil (3 mg/kg) | 171.09 ± 78.08 ◊ * | 6.27 ± 1.27 ◊ # | 0.00 ± 0.00 # |

Notes:
1 - LFM, latency until the first mount,
2 - MN, the number of mounts
3 - EN, the number of ejaculations.
4 - # - differences are significant vs. background in the same test ($p < 0.05$, Mann-Whitney U-test)
5 - * - differences are significant vs. control in the same test ($p < 0.05$, Mann-Whitney U-test)
6 - ◊ - differences are significant in comparison within the group with the first test ($p < 0.05$, Mann-Whitney U-test)

The data presented in Tables 5 and 6 showed that rats of late reproductive age had reduced indices of sexual activity (an increase in latency until the first mount, a decrease in the number of mounts, and ejaculating animals were not detected, Table 5). In animals that received Treamid, the latency until the first mount was significantly reduced, the number of mounts increased, and ejaculatory animals were registered (Table 6). The administration of Sildenafil improved the sexual activity of animals, but to a lesser extent: the latency until the first mount decreased, the number of mounts increased, but ejaculating animals were not registered.

Thus, Treamid is an effective agent for recovery of copulatory activity in animals of late reproductive age.

The results of studies carried out on presenile animals (19 months) are presented in Table 7.

TABLE 7

Indices of copulatory behavior of male rats of presenile age (19 months) before administration and 14 days after administration of Treamid

| Age of animals (months) | Group name | First test (before administration of drugs) | | | Second test (after 14-day administration course) | | |
|---|---|---|---|---|---|---|---|
| | | LFM (sec) | MN (abs.) | EN (abs.) | LFM (sec) | MN (abs.) | EN |
| 3 | Background | 134.80 ± 28.31 | 8.90 ± 1.66 | 0.44 ± 0.18 | 66.70 ± 10.56 | 10.20 ± 1.58 | 0.20 ± 0.13 |
| 19 | Control | 318.55 ± 100.11 # | 4.00 ± 0.83 # | 0.00 ± 0.00 # | 283.91 ± 106.39 | 6.09 ± 1.52 | 0.00 ± 0.00 # |
| | Treamid (5.0 mg/kg) | 310.27 ± 94.59 # | 4.27 ± 1.04 # | 0.00 ± 0.00 # | 297.20 ± 117.04 | 7.90 ± 1.45 ◊ | 0.20 ± 0.13 ◊ * |

Notes:
1 - LFM, latency until the first mount,
2 - MN, the number of mounts
3 - EN, the number of ejaculations.
4 - # - differences are significant vs. background in the same test ($p < 0.05$, Mann-Whitney U-test)
5 - # - differences are significant vs. control in the same test ($p < 0.05$, Mann-Whitney U-test)
6 - ◊ - differences are significant in comparison within the group with the first test ($p < 0.05$, Mann-Whitney U-test).

The data presented in Table 7 show that in the animals of the control group, the latency until the first mount was increased, the number of mounts decreased, and the ejaculating animals were absent. After the 14-day administration of Treamid at a dose of 5 mg/kg, an increase in the number of mounts was significant, and ejaculating animals were registered.

Thus, the study showed that Treamid, when administered at a dose of 5 mg/kg for 14 days, led to the recovery of the copulatory activity in rats of late and presenile age.

a dose of 5 mg/kg has a stimulating effect on the sexual motivation of male rats of the late reproductive period. It should be noted that the preference score in this group of rats was statistically significantly different from that in the intact rats, i.e. in "young" animals.

In the group of rats treated with reference drug Sildenafil (3 mg/kg), the average time spent near a female rat did not increase. However, the time spent near the social stimulus increased. The preference score did not differ significantly

TABLE 8

Indices of sexual motivation of male rats of late reproductive age before and 14 day after administration of Treamid

| Age of animals (months) | Group | A, sec | B, sec | PS, s.u. | Second test, after administration of the test compound | | |
|---|---|---|---|---|---|---|---|
| | | | | | A, sec | B, sex | PS, s.u. |
| 3 | Background | 240.10 ± 26.38 | 85.30 ± 25.78 | 0.74 ± 0.07 | 261.60 ± 36.58 | 64.00 ± 7.32 | 0.77 ± 0.04 |
| 14 | Control | 106.92 ± 21.20 # | 113.75 ± 25.31 | 0.48 ± 0.07 # | 157.73 ± 46.24 # | 170.00 ± 42.18 # | 0.49 ± 0.09 # |
| | Treamid (5 mg/kg) | 132.30 ± 23.69 # | 113.60 ± 13.77 | 0.51 ± 0.06 # | 154.00 ± 41.83 # ◊ | 95.60 ± 29.66 | 0.64 ± 0.09 ◊ |
| | Sildenafil (3 mg/kg) | 166.83 ± 26.27 # | 113.58 ± 22.60 | 0.59 ± 0.06 # | 143.18 ± 48.64 # | 231.18 ± 62.80 # | 0.41 ± 0.12 # |

Notes:
1 - A, the time spent in the "sexual" stimulus zone,
2 - B, the time spent in the "social" stimulus zone,
3 – PS, preference score = $\frac{A}{A+B} \times 100$,
4 - the number of crossed squares,
5 - # - differences are significant vs. background in the same test ($p < 0.05$, Mann-Whitney U-test)
6 - # - differences are significant vs. control in the same test ($p < 0.05$, Mann-Whitney U-test)
7 - ◊ - differences are significant in comparison within the group with the first test ($p < 0.05$, Mann-Whitney U-test).

The data presented in Table 8 show that the time spent near the sexual stimulus and the preference score in the control were lower compared to those in the intact animals (the first test). The obtained data testify that the model of suppression of sexual motivation provided by the use of 14-month animals was obtained in the control. This allows testing of the drug.

The determined time spent by the studied male rats in the sexual stimulus zone and the calculated preference score before the beginning of the experiment showed that the values of these indices in the experiment and in the control did not differ significantly from each other. This confirms the correctness of the conducted randomization and the fact that female rats did not avoid males and were susceptible to them.

An analysis of the average time spent by the intact male rats (background) in the zones of social and sexual stimuli and the preference score obtained in the first and second tests showed that they did not differ statistically significantly from each other. This indicates the stability of the motivational behavior of male rats used in the experiment, and confirms the literature data that sexual motivation remains at the same level for a certain period of time (up to 55 days).

An analysis of the studied indices of the first and second tests of the rats in the control group showed that the level of sexual motivation of the animals remained unchanged.

When Treamid was administered at a dose of 5 mg/kg, the time spent near the "sexual" stimulus increased in comparison with that in the same animals before the administration of the drug. At the same time, the time spent in the "social" stimulus zone decreased (by 2 times) compared with the control. The preference score was statistically significantly higher than in the first test and reached 0.64±0.09. The obtained data indicate that the administration of Treamid at from the initial level. This indicates that Sildenafil had no effect on the sexual motivation of male rats.

Thus, the test of Treamid as a stimulant of sexual motivation of male rats of mature reproductive age (14 months) showed that the compound stimulates sexual motivation of animals of late reproductive age. The effect is manifested at a dose of 5 mg/kg; the optimal period of therapy is 14 days.

The reference drug, Sildenafil, did not show activity in the test for sexual motivation. In the test for copulatory activity, its effect was insufficiently pronounced and short-lived.

Example 5

Study of the Effectiveness of Treamid for Recovery of Copulatory Activity of Male Rats in Intact Animals Under Conditions of Seasonal Suppression of Copulatory Activity Seasonal suppression of reproductive activity was simulated by carrying out the experiment in the winter period (end of December). As a background group, intact animals (3 months of age) were tested in June.

The experiments were carried out on 27 male Wistar rats of reproductive age (3 months). Treamid at a dose of 5 mg/kg and reference drug Sildenafil (at a dose of 3 mg/kg) were administered intragastrically 2 times a week, once daily for 15 days. The sexual activity was estimated by the pair-test of sexual behavior. The test was carried out twice: before administration and one hour after the last administration of Treamid. The rats of the control groups receiving the solvent were tested at the same time as the animals of the experimental groups.

The experiment also comprised the use of female rats in the estrus stage caused by a preliminary 4-fold injection of the Synestrel. The effectiveness of Treamid was estimated by the following indices: latency until the first mating attempt (LFM), the number of mating attempts (MN), and the number of ejaculations (EN). The obtained data were compared with those of the same animals before the administration of the tested compound and with the data of the control group (the second test).

The results of the comparison of the copulatory activity of the animals in the control and experimental groups are presented in Table 9.

TABLE 9

Effect of Treamid on the indices of copulatory behavior of male rats on the model of its seasonal suppression

| | | | | First and secondary tests | | |
|---|---|---|---|---|---|---|
| No | LFM, sec | the number of mounts, abs. | the number of ejaculations, % | LFM, sec | the number of mounts, abs. | the number of ejaculations, % |
| Control | 466.56 ± 114.21 | 3.44 ± 1.23 | 0% | 331.11 ± 116.11 | 4.56 ± 1.28 | 11% |
| Treamid 5.0 mg/kg | 462.00 ± 117.81 | 3.67 ± 1.34 | 0% | 251.33 ± 103.86♦ | 6.56 ± 1.68 | 33%♦ |
| Viagra | 473.00 ± 137.58 | 3.33 ± 1.27 | 0% | 308.22 ± 117.73 | 5.67 ± 1.76 | 0% |

♦differences are significant vs. the first test, i.e. before and after the administration of the derivative.

The results of testing male rats of the background group showed that the animals were characterized by sufficiently high and stable rates of sexual activity. The average latency until the first mount was 114 seconds, the number of mounts was 14.7, and the number of matings was 0.33. A comparison of the tested indices in the "summer" time with that in the "winter period" shows that the latency until the first mating attempt increased by 4 times, and the number of mating attempts decreased by 3.4 times ($P \leq 0.05$). In addition, in the winter there was no ejaculation in the males of the control group ($P \leq 0.05$).

The administration of Sildenafil did not have a significant effect on the sexual behavior of the male rats under seasonal suppression of their sexual activity. Before and after its administration, the studied indices did not differ within the group and from those in the control group. The results of monitoring the sexual activity of the male rats treated with Treamid at a dose of 5 mg/kg showed that the latency until the first mount significantly decreased after administration, by 1.8 times, compared to that before testing, which indicates a stimulating effect of the drug on the sexual attraction centers and, to a certain extent, on the copulatory activity. The total number of mating attempts increased by 1.8 times, but the differences were statistically insignificant. The calculated number of animals in the group with observed ejaculations showed that after the administration of Treamid, ejaculations were detected in 33%, while before the administration of the drug, these animals did not ejaculate ($P \leq 0.05$).

Thus, the obtained data are convincing evidence of the ability of Treamid to restore the sexual activity in male rats under conditions of seasonal reduction in their sexual activity.

Example 6

Study of the Effectiveness of Treamid for Regeneration and Normalization of the Structure of Prostate Tissue in Chronic Abacterial Prostatitis (CAP) or Benign Prostatic Hyperplasia (BPH)

This is manifested in a decrease in the severity of the morphological changes typical in these diseases. CAP was simulated by suturing the ventral lobe of the gland with a silk thread, and BPH was simulated by the administration of Sulpiride. The reference drug was Prostamol Uno.

Treamid were administered intragastrically to animals with CAP at a dose of 0.5 mg/kg for 15 days.

Animals with BPH received Teramide intragastrically for 2 months at a dose of 0.5 mg/kg.

1. Study of the Effectiveness of Treamid for Regeneration and Normalization of the Structure of Prostate Tissue on the Model of Chronic Abacterial Prostatitis (CAP)

Experiments were performed on 40 male Wistar rats (3 months of age). To simulate chronic abacterial prostatitis, the ventral lobe of the prostate was sutured with a silk thread (under anesthesia). The model of benign prostatic hyperplasia (BPH) was simulated in rats by inducing hyperprolactinaemia, for which male rats were intraperitoneally injected with Sulpiride at a dose of 40 mg/kg every day for 2 months (Eglonil, Sanofi Winthrop Industry, France).

One month after the surgery, the animals of the experimental group were intraperitoneally administered Treamid at a dose of 0.5 mg/kg once daily for 15 days. At the end of the administration course, the animals were weighed and euthanized in a $CO_2$ chamber. The ventral lobe of the gland was then dissected, weighed, and its volume was measured, followed by the calculation of a weight coefficient, and subjected to morphological analysis. For this purpose, the prostate was fixed in formalin and poured into paraffin. Paraffin sections of a thickness of 5 μm were stained with hematoxylin-eosin according to Van Gieson on the connective tissue, to calculate the relative area of the epithelium. Further, the severity of atrophic processes and developing sclerosis was qualitatively assessed. The assessment was carried out on standard area of the gland section by using a computer graphic analysis (micrographs of 10 serial visual fields performed by an AxioCam Erc5s camera mounted on an AxioLab A1 microscope (×10 lens, ×10 eyepiece), with an image transfer software of "AxioVision LE", Carl Zeiss). The area occupied by secretory sites, collagen fibers of connective tissue septa was determined. The effectiveness of the drug was estimated by the following criteria: lower intensity of morphological symptoms of chronic abacterial prostatitis (atrophy and sclerosis): the area occupied by secretory sections, collagen fibers of connective tissue septa.

The results of the study are presented in Tables 10-11.

TABLE 10

An effect of Treamid on the weight and volume of the anterior lobe of the prostate gland in rats suffered from CAP

| Group | Animal weight at the end of the experiment | Weight of the anterior lobe of the prostate gland, mg | Weight coefficient of the anterior lobe of the prostate gland, mg/g | Volume of the anterior lobe of the prostate gland, cm$^3$ |
| --- | --- | --- | --- | --- |
| Background | 517.40 ± 34.24 | 682.00 ± 91.56 | 1.33 ± 0.20 | 0.66 ± 0.10 |
| Control | 454.40 ± 36.34 | 536.00 ± 111.29 | 1.15 ± 0.22 | 0.49 ± 0.11 |
| Treamid at a dose of 0.5 mg/kg | 497.60 ± 34.03 | 976.00 ± 226.62 | 1.97 ± 0.47 | 0.90 ± 0.20 |
| Prostamol Uno, 50 mg/kg | 518.40 ± 24.82 | 728.00 ± 61.27 | 1.40 ± 0.09 | 0.71 ± 0.06 |

Notes:
1 - # - differences are significant vs. background (p < 0.05, Mann-Whitney U-test)
2 - # - differences are significant vs. control (p < 0.05, Mann-Whitney U-test)
3 - Ω - differences are significant vs. the group of Prostamol Uno (p < 0.05, Mann-Whitney U-test)

TABLE 11

Morphometric parameters of the anterior part of the prostate gland in rats suffered with chronic aseptic prostate inflammation, %

| Group | Area of collagen fibers | Area of the acinar epithelium |
| --- | --- | --- |
| Background | 0.66 ± 0.27 | 33.08 ± 4.12 |
| Control | 3.12 ± 0.63# | 21.89 ± 2.45# |
| Treamid at a dose of 0.5 mg/kg | 2.64 ± 0.12# | 26.33 ± 2.63 |
| Prostamol Uno, 50 mg/kg | 4.12 ± 0.74# | 24.84 ± 3.62# |

Notes:
1 - #differences are significant vs. background (p < 0.05, Mann-Whitney U-test)
2 - #differences are significant vs. control of the same test (p < 0.05, Mann-Whitney U-test)
3 - Ω - differences are significant vs. the group of Prostamol Uno (p < 0.05, Mann-Whitney U-test)

The presented experimental data show that the weight of the gland, its weight coefficient and volume in all the compared groups did not differ significantly from each other (Table 10). Morphological analysis (Table 11) showed that in the prostate gland of the control rats, the area of the acinar epithelium significantly decreased (atrophy) and the area of collagen fibers increased (sclerosis). The administration of Treamid to male rats at a dose of 0.5 mg/kg resulted in an increase (by 22%) in the area of the acinar epithelium. The value of this parameter was not significantly different from the background values, while in the control it was significantly lower compared to the background. The area of collagen fibers tended to decrease. When the obtained data were compared with those obtained for the administration of Prostamol Uno, it was found that Prostamol Uno had no effect on the area of the acinar epithelium. The obtained data allow the conclusion that the use of Treamid at a dose of 0.5 mg/kg in rats with CAP promotes the regeneration of prostate epithelial tissue. This is expressed in a decrease in the severity of atrophic processes. The latter, obviously, will lead to an increase in the functional activity of the acinar epithelium and will promote restoration of qualitative characteristics of the ejaculate.

2. Study of the Effectiveness of Treamid for Regeneration and Normalization of the Structure of Prostate Tissue on the Model of Benign Prostatic Hyperplasia (BPH)

The ability of Treamid to normalize the structure of the prostate gland was studied in the presence of administration of Sulpiride. For this purpose, Treamid was administered intragastrically for 2 months at a dose of 0.5 mg/kg simultaneously with Sulpirid. The control animals received a solvent (2% starch mucus) in an equivalent volume. The animals of the comparison group were injected intragastrically with a solution of Prostamol Uno at a dose of 50 mg/kg. At the end of the administration course, the animals were weighed and euthanized in a $CO_2$ chamber. Sulpiride is known to cause the development of BPH in the lateral lobe of the gland in rats [Van Coppenolle Fabien, Christian Slomianny, Francoise Carpentier Effects of hyperprolactinemia on rat prostate growth: evidence of androgeno-dependence.//Physiol. Endocrinol. Metab. —2001. —P. 120-129]. In this regard, this lobe was dissected. Its weight, weight coefficient, and volume were determined. Further, it was subjected to a morphological analysis. The lateral lobe of the prostate gland was fixed in 10% formalin and poured into paraffin, followed by preparation of sections of a thickness of 5 μm. Deparaffined sections of the gland were stained with hematoxylin and eosin. On the histological sections, the presence of proliferative centers and daughter acini were determined per standard section area. In addition, the area of the epithelial and stromal structures was measured on the standard area of a histological section. These parameters were determined by using a computer graphic analysis on the standard area of a histological section (micrographs of 10 serial visual fields performed by an AxioCam Erc5s camera mounted on an AxioLab A1 microscope (×10 lens, ×10 eyepiece), with an image transfer software of "Axio-Vision LE", Carl Zeisis). The stromal-epithelial ratio was defined as a ratio of the area of stroma to the area of epithelium.

The effectiveness of the test compound was estimated by the following criteria: lower intensity of morphological symptoms of benign prostatic hyperplasia: —a decrease inthe number of proliferation centers and daughter acini, and a decrease in the area of the epithelium.

The results of the studies are presented in Tables 12-16.

TABLE 12

Body weight; weight and volume of the lateral lobe of the prostate gland of rats suffered from benign hyperplasia (BPH)

| Group name | Animal weight at the end of the experiment, g | Weight of the lateral lobe of the prostate gland, mg | Weight coefficient of the lateral lobe of the prostate gland, mg/g | Volume of the lateral lobe of the prostate gland, $cm^3$ |
|---|---|---|---|---|
| Background | 559.00 ± 13.39 | 74.00 ± 9.27 | 0.13 ± 0.02 | 0.16 ± 0.02 |
| Control drug | 564.17 ± 28.17 | 363.33 ± 31.69# | 0.59 ± 0.08# | 0.67 ± 0.07# |
| Treamid at a dose of 0.5 mg/kg | 540.673 ± 42.78 | 381.67 ± 70.30# | 0.69 ± 0.12# | 0.62 ± 0.14# |
| Prostamol Uno | 496.20 ± 20.34# | 396.00 ± 82.98# | 0.81 ± 0.18*# | 0.70 ± 0.17# |

Notes:
1 - #differences are significant vs. background in the same test ($p < 0.05$, Mann-Whitney U-test)
2 - #differences are significant vs. control in the same test ($p < 0.05$, Mann-Whitney U-test)
3 - Ω - differences are significant vs. the group of Prostamol Uno ($p < 0.05$, Mann-Whitney U-test)

TABLE 13

Relative area (%) of the acinar epithelium on the standard area of a section of the lateral lobe of the prostate gland of male rats with hyperplasia

| | Group | | | |
|---|---|---|---|---|
| No of animal | Background | Control | Treamid at a dose of 0.5 mg/kg | Prostamol Uno |
| 1 | 16.24 | 18.87 | 8.61 | 24.02 |
| 2 | 7.11 | 17.02 | 10.26 | 18.02 |
| 3 | 21.33 | 23.10 | 14.09 | 16.63 |
| 4 | 13.78 | 21.49 | 16.30 | 29.10 |
| 5 | 18.67 | 22.45 | 20.19 | 20.05 |
| M ± m | 15.43 ± 2.43 | 20.59 ± 1.15 # | 13.89 ± 2.08 * | 21.56 ± 2.26 |

Notes:
here and below

1 - # - differences are significant vs. background of the same test ($p < 0.05$, Mann-Whitney U-test)
2 - # - differences are significant vs. control of the same test ($p < 0.05$, Mann-Whitney U-test)
3 - Ω - differences are significant vs. the group of Prostamol Uno ($p < 0.05$, Mann-Whitney U-test)

TABLE 14

The number of structures (abs.) consisting of 2-3 glandules tightly adjacent to each other, on the standard area of a section of the lateral lobe of the prostate gland of male rats with hyperplasia

| | Group | | | |
|---|---|---|---|---|
| No of animal | Background | Control | Treamid at a dose of 0.5 mg/kg | Prostamol Uno |
| 1 | 0 | 3 | 0 | 6 |
| 2 | 0 | 0 | 1 | 3 |
| 3 | 0 | 2 | 3 | 0 |
| 4 | 0 | 3 | 4 | 0 |
| 5 | 0 | 3 | 0 | 0 |
| M ± m | 0.00 ± 0.00 | 2.20 ± 0.58# | 1.60 ± 0.81# | 1.80 ± 1.20 |

TABLE 15

The number of daugter proliferative centers (abs.) on the standard area of a section of the lateral lobe of the prostate gland of male rats with hyperplasia

| | Group | | | |
|---|---|---|---|---|
| No of animal | Background | Control | Treamid at a dose of 0.5 mg/kg | Prostamol Uno |
| 1 | 0 | 8 | 3 | 1 |
| 2 | 0 | 3 | 3 | 2 |
| 3 | 0 | 4 | 1 | 1 |
| 4 | 0 | 3 | 0 | 3 |
| 5 | 0 | 3 | 1 | 2 |
| M ± m | 0.00 ± 0.00 | 4.20 ± 0.97# | 1.60 ± 0.60# | 1.80 ± 0.37#* |

TABLE 16

Relative area (%) of the stroma on the standard area of a section of the lateral lobe of the prostate gland of male rats with hyperplasia

| | Group | | | |
|---|---|---|---|---|
| No of animal | Background | Control | Treamid at a dose of 0.5 mg/kg | Prostamol Uno |
| 1 | 32.15 | 46.03 | 51.82 | 49.97 |
| 2 | 40.26 | 45.87 | 48.61 | 51.21 |
| 3 | 23.27 | 45.78 | 45.59 | 48.39 |
| 4 | 36.55 | 40.40 | 44.14 | 41.84 |
| 5 | 41.42 | 39.53 | 38.12 | 40.93 |
| M ± m | 34.73 ± 3.29 | 43.52 ± 1.46# | 45.66 ± 2.30# | 46.47 ± 2.13#* |

Notes:
1 - #differences are significant vs. background of the same test ($p < 0.05$, Mann-Whitney U-test)
2 - #differences are significant vs. control of the same test ($p < 0.05$, Mann-Whitney U-test)
3 - Ω - differences are significant vs. the group of Prostamol Uno ($p < 0.05$, Mann-Whitney U-test)

The presented experimental data showed that the weight of the prostate gland and its weight coefficient in all the compared groups did not differ significantly from each other (Table 12). A quantitative morphological analysis showed that the administration of Sulpiride resulted in a significant increase in the area of the acinar epithelium in the standard section area by 33% (Table 13), which is evidence of its enhanced proliferation. Morphologically it is expressed, first of all, in an exuberant growth of papillary projections of the epithelium. In the prostate of the rats receiving Sulpiride, there were the structures that consisted of 2-3 glandules adjacent to each other (Table 14). In addition, about 3 to 8 daughter proliferation centers were registered on the standard section area (Table 15). Relative area of stromal structures significantly increased, by 22%.

The symptoms of BPH were less pronounced in case of administering Treamid. Thus, a significant decrease in the area of the acinar epithelium (Table 14) and a decrease in the number of daughter proliferative centers (Table 15) were observed in the prostate of the animals of this group. These data indicate the presence of antiproliferative properties of the test compound. Reference drug Prostamol Uno also had a therapeutic effect. Thus, its administration to male rats receiving Sulpiride resulted in a decrease in the number of daughter proliferative centers (Table 15). However, its effectiveness was lower than that of the test compound, as evidenced by the ability of the latter to reduce the area of the epithelium, which was not detected for the administration of the reference drug.

Thus, Treamid at a dose of 0.5 mg/kg effectively restores the morphological state of the prostate gland in the presence of the administration of Sulpiride, which is manifested in a decrease in the severity of BPH symptoms in the experimental animals. Its effectiveness exceeds the effectiveness of the reference drug, Prostamol Uno.

Example 7

Study of the Effectiveness of Treamid for Strengthening the Processes of Reparative Regeneration of Testicular Tissue and the Treatment of Testicular Failure Caused by Depletion of Proliferative Pool of Spermatogenesis The latter was simulated by a single injection of cytostatic drug Paclitaxel (Mitotax, Dr. Reddy's, India) to male rats (3 months of age). The choice of the drug was due to the fact that it is one of the medications that damage the precursors of spermatogenesis—stem cells.

Paclitaxel was administered to the animals of the control and test groups once intravenously at the maximum tolerated dose of 7.6 mg/kg. Treamid was administered to the animals of the experimental groups intragastrically at a dose of 5 mg/kg in the form of a suspension in 2% starch mucus for 15 days a month after the administration of Paclitaxel. The control animals received an equivalent volume of the solvent (2% starch mucus), instead of the test compound.

The effect of Treamid on the deep reserve of regeneration of spermatogenic tissue was studied by a method for evaluating the colony-forming ability, allowing the determination of the number of committed spermatogenic stem cells [A. J. Richards, G. C. Enders, J. L Resnick//Biol. Reprod. —1999. —Vol. 61. —P. 1146-1151.].

On Day 1 (in 24 hours), as well as on Day 45 and Day 65 after the administration of Paclitaxel, the animals were euthanized, and the preparations of their testes were made. Further, the content of progenitor cells of spermatogenesis in the testes was determined by an in vitro cloning method. The progenitor cells of the studied organ were cultured by using an underlayer that was represented by adherent fraction cells. The underlayer of adherent cells was prepared under conditions of 5% $CO_2$ and at 37° C. by homogenization of one testis of an intact animal in DMEM medium and washing by centrifugation (1500 rpm, 10 min). The resulting slurry of cells was then divided into an adherent and a nonadherent fraction. For this, 0.5 ml of the prepared suspension of cells was placed in each well of a 24-well plate at a concentration of $1\times10^6$/ml in a culture medium for precursor cells and further incubated for 1 hour in a $CO_2$ incubator at 37° C., 5% $CO_2$ and 100% air humidity. After incubation, a nonadherent portion of the cells was harvested. Medium for culturing spermatogenic progenitor cells were placed in an amount of 0.5 ml in wells containing a fraction of adherent cells and incubated for 7 days in a $CO_2$ incubator at 37° C., 5% $CO_2$ and 100% air humidity. After 7 days, the culture medium was replaced, followed by layering nonadherent cells of the testes of experimental animals over the resulting stroma. For this purpose, according to the procedure described above, the cells were divided into an adhesive and a nonadherent fraction. The homogenate of the organ was incubated in Petri dishes for 1 hour in a $CO_2$ incubator at 37° C., 5% $CO_2$ and 100% air humidity. Then, the nonadherent fraction of cells was collected, and the number of cells (cells/ml) was counted in the Goriaev chamber. Nonadherent cells were layered at a concentration of $2\times10^5$/ml over the resulting stroma in a volume of 0.5 ml per well. Incubation lasted for 7 days in a $CO_2$ incubator at 37° C., 5% $CO_2$ and 100% air humidity. After the incubation, the number of colony-forming units, spermatogenic (CFU-Sp)—clusters of more than 30 cells of round shape and of various diameters—was counted. The criterion for the effectiveness of the used agent was a significant increase in the number of cells giving rise to CFU-Sp in the testicular tissue of test animals compared with that in the control.

The colony-stimulating activity of the cells of the microenvironment of spermatogenic tissue (production of humoral regulators of spermatogenesis by Sertoli cells) was determined as follows. The above-described procedure was used to prepare a testis homogenate from which an adherent fraction of cells was isolated. The adherent cells were cultured for 24 hours in complete culture medium at 37° C., 5% $CO_2$ and 100% air humidity. A day later, the supernatant was collected, which was stored at a temperature of 20° C. The level of humoral factors of spermatogenesis in the supernatant was tested by the test system of CFU-Sp of the testes of intact rats. The obtained results were expressed by the number of colonies grown from the number of layered nonadherent cells ($10^5$ cells/well).

The effectiveness of Treamid was estimated by a significant increase in the colonies grown from the cells of the test system under the action of the supernatant cells of the test animals compared with that in the control.

The precursor cells of the studied organ were cultured by using an underlayer (represented by the cells of the adherent fraction) prepared in advance in a 96-well plate, as described above.

Further, a nonadherent cell fraction of spermatogenic tissue was isolated from the two groups of animals (intact animals and animals received Paclitaxel intravenously 24 hours prior to the study) and was transferred to the resulting underlayer in complete culture medium (80% DMEM, 20% FCS, L-glutamine, antibiotics, heparin) at a concentration of $2\times10^5$/ml. Prior to the incubation in the complete culture medium, Treamid was added at a concentrations of 1 ng/ml, 3 ng/ml, 10 ng/ml, 30 ng/ml, 100 ng/ml, 300 ng/ml and 1000 ng/ml. The incubation lasted for 7 days in a $CO_2$ incubator at 37° C., 5% $CO_2$ and 100% air humidity. After the incubation, the number of colony-forming units, spermatogenic (CFU-Sp)—clusters of more than 30 cells of round shape and of various diameters—was counted.

The effectiveness of Treamid was estimated by a significant increase in the number of cells giving rise to CFU-Sp in the culture with the addition of the test compound, compared to that in the control.

Morphological and functional state of the spermatogenic tissue was assessed to obtain an additional confirmation of the efficiency to stimulate the formation of committed stem cells.

It was estimated by the following indices: the number of cells in the spermatogonial population, the average number of Sertoli cells, the degree of maturity of the spermatogenic layer, the number of Leydig cells, the endocrine activity of the testis, the total number of sperm cells per epididymis, and the percentage of motile sperm forms. For this, in euthanasia on Day 45, Day 65, and Day 90 of the experiment, the tail part of epididymis and testis were isolated at dissection. The epididymis of one testis was homogenized in a warm (37° C.) physiological saline, and the number of motile sperm forms was determined in the suspension of the epididymis cells. The total number of sperm cells per epididymis (TNS) was calculated by using a homogenized cell suspension of the second epididymis in a dosage amount of physiological saline using a leukocyte-count pipette and Goryaev chamber.

A morphological assay of the testes of rats was performed by fixation thereof in Carnoy's fluid and by preparing paraffin sections. Deparaffined sections of a thickness of 5 μm were stained with hematoxylin-eosin. The number of cells in the spermatogonial population, the number of Sertoli cells, and the number of Leydig cells were counted on the testis section, and the endocrine activity of Leydig cells was determined. The degree of maturity of the spermatogenic layer was calculated based on the count of Sertoli cells. The calculation was carried out according to the formula for the experimental groups: y=5.95-0.18x; for the group of intact animals: y=6.7-0.23x, where x is the average number of Sertoli cells in the cross-section of the convoluted seminiferous tubule, and y is the index characterizing the degree of maturity of the spermatogenic layer. When choosing the time for studies, the duration of spermatogenesis in rats was taken into account, which was one and a half months. The duration of 45 and 65 days after administration of Paclitaxel corresponds to the manifestation of effects on the spermatogonial cell population.

The criteria for stimulation of the process of regeneration of the testicular tissue were: an increase in the number of cells in the spermatogonial populations, the number of Sertoli cells, a decrease in the degree of maturity of the spermatogenic layer, and an increase in the productivity of spermatogenesis. The criterion of the functional activity of sperm cells is the percentage of their motile forms.

The results of the studies are presented in Tables 17 and 18.

TABLE 17

Dynamics of the content of CFU-Sp in the rat testes in administration of Paclitaxel and the test compound, Treamid

| Time of the study, days | Group | CFU-Sp, per $2 \times 10^5$ (M; SD, n = 10) |
|---|---|---|
| Background | | 5.8; 0.70 |
| Day 1 | Paclitaxel | 3.5; 0.69* |
| Day 45 | Paclitaxel | 2.9; 0.48* |
| | Treamid | 4.2; 0.29# |
| Day 65 | Paclitaxel | 2.3; 0.42* |
| | Treamid | 3.4; 0.4# |

Notes:
1. *difference in the indices between the intact control (background) and test groups was significant (p < 0.05, Mann-Whitney U-test)
2. #differences between the control (Paclitaxel) and test groups were significant (p < 0.05, Mann-Whitney U-test)

The presented experimental data showed that the study of the content of the precursors for spermatogenic tissue in the rat testes after the administration of Paclitaxel revealed a statistically significant decrease in the number of cells giving rise to colonies (CFU-Sp) on Day 1, Day 45 and Day 65 of the experiment (Table 17). Thus, at the end of the experiment, the number of colony-forming cells decreased by almost 40%.

The administration of Treamid was associated with a significant increase (by 44-48%) in the number of colony-forming cells in all investigated time points (on Day 45 and Day 65 of the experiment) compared with the cytostatic control (Table 17).

TABLE 18

Changes in the levels of colony stimulating activity of conditioned media of testis cells ($\times 10^5$ cells) in administration of Paclitaxel and the test compound, Treamid

| Time of the study, days | Group | CFU-Sp, per $2 \times 10^5$ (M; SD, n = 10) |
|---|---|---|
| Background | | 9.25; 0.67 |
| Day 1 | Paclitaxel | 3.0; 0.53* |
| Day 45 | Paclitaxel | 6.37; 0.32* |
| | Treamid | 6.12; 0.29* |
| Day 65 | Paclitaxel | 3.25; 0.45* |
| | Treamid | 5.88; 0.52*# |

Notes:
1. *differences in the index with the intact control was significant (p < 0.01, Mann-Whitney U-test),
2. #differences between the control (Paclitaxel) and test groups were significant (p < 0.01, Mann-Whitney U-test)

The study of the mechanisms for reducing colony-forming activity of stem cells after administration of Paclitaxel showed a decrease in the production of humoral factors by the cells of the microenvironment of spermatogenic tissue, stimulating the growth of the colonies from precursors for spermatogenic tissue on Day 1, Day 45 and Day 65 of the study (Table 18). The most significant suppression of hormonal regulation (by 2.8 and 3 times) of the colony formation of committed spermatogenic cells was detected on Day 1 and Day 65 of the experiment. The obtained data indicate that Paclitaxel had not only a direct toxic effect on the stem spermatogonia but also suppressed the functional activity of microenvironment cells, thereby reducing their stimulating effect on the renewal of cells constituting a deep reserve of the spermatogenic tissue. This indicates the suppression of the hormonal regulation of the functions of stem spermatogonia under the action of Paclitaxel.

On Day 65 of the experiment, a statistically significant increase (by 80%) of the secretory activity of the microenvironment cells was observed in the group of rats treated with Treamid compared to the control (Table 18). This indicates the activation of the functional state of the microenvironment cells under the action of Treamid.

The direct action of Treamid on the precursors for spermatogenic tissue was studied in vitro by addition of Treamid to the cell culture at concentrations of 1, 30, 100, and 1000 ng/ml.

The results of the experiment are presented Table 19.

TABLE 19

Action of Treamid on the growth of colonies from CFU-Sp in in vitro addition (M; SD, n = 6)

| The concentration of Treamid in the culture | CFU-Sp per $4 \times 10^4$ nuclears | |
|---|---|---|
| | Cells of the testes of intact rats | Cells of rat testes on Day 1 after IV administration of Paclitaxel |
| Control | 7.0 ± 0.58 | 2.67; 0.33* |
| Treamid (1 ng/ml) | 6.83 ± 0.48 | 6.83; 0.60# |
| Treamid (30 ng/ml) | 6.0 ± 0.36 | 5.17; 0.65# |
| Treamid (100 ng/ml) | 8.50 ± 0.42* | 4.67; 0.61# |
| Treamid (1000 ng/ml) | 11.67 ± 1.81* | 5.67; 0.33# |

Notes:
1 - ◊ - differences are significant vs. intact control (p < 0.05, Mann-Whitney U-test);
2 - #differences are significant vs. cytostatic control (p < 0.05, Mann-Whitney U-test).

As a result of determining the content of the precursors for spermatogenic tissue in the rat testes after the administration of Paclitaxel, a statistically significant (Table 19) decrease in colony formation was observed on Day 1, which corresponded to the previously obtained data.

When Treamid was added (at concentrations of 100 and 1000 ng/ml) to a complete culture medium containing the precursors for spermatogenic tissue of intact animals, a significant increase in the content of CFU-Sp was registered.

The study of the direct action of Triamide in vitro on the formation of spermatogenic colonies from cells derived from rat testes on Day 1 after intravenous administration of Paclitaxel showed an increase in colony formation under the action of the test compound, when administered, at all the tested concentrations (Table 19).

The obtained data indicate that Treamid has the ability to directly stimulate the functional activity of progenitor cells for spermatogenic tissue.

Thus, the administration of Paclitaxel led to a decrease in the regenerative potential of the testis, which is expressed in a decrease in the number of committed colony-forming spermatogenic cells. This is due not only to the direct toxic effects of Paclitaxel on the sources of the proliferative pool of spermatogenesis, but also to the suppression of humoral factors that stimulate proliferation of these cells. The administration of Treamid increased the regenerative potential of the tissue. In addition, Treamid not only directly stimulated the formation of new sources of proliferative pool of spermatogenesis (stem cells), but also enhanced the effect of humoral factors stimulating their formation.

When studying the morphological and functional state of spermatogenic tissue 45 days after the start of the experiment, it was found that the administration of Paclitaxel resulted in a significant decrease (by more than 30%) in the number of cells in the spermatogonial population, spermatogenesis productivity, as judged by TNS, decreased compared to the background more than by 40% (Table 19).

TABLE 20

Assessment of spermatogenesis in rats on Day 45 after administration of Paclitaxel

| Group | The average number of spermatogonia (abs.) | The average number of Sertoli cells (abs.) | The degree of maturity of the spermatogenic layer (standard units) | Total number of sperm cells (million) | Number of motile sperm cells (%) |
|---|---|---|---|---|---|
| Background (intact animals) | 18.47 ± 0.28 | 1.07 ± 0.03 | 6.45 ± 0.01 | 213.00 ± 0.81 | 80.05 ± 3.20 |
| Control (Paclitaxel) | 11.88 ± 0.35* | 1.51 ± 0.02* | 5.68 ± 0.00* | 125.00 ± 5.82* | 63.68 ± 1.50* |
| Experiment: Paclitaxel + Treamid | 14.56 ± 0.19*# | 1.61 ± 0.03*# | 5.66 ± 0.01# | 146.00 ± 9.53* | 71.57 ± 3.19# |

Note:
*differences are significant vs. background
differences are reliable vs. control.

Simultaneously with a decrease in the total number of mature germ cells, there was a statistically significant decrease in the percentage of their motility. Thus, 45 days after the administration of Paclitaxel, testicular failure was observed in the form of pathospermia, which is one of the causes of male infertility. The term of 45 days corresponds to the manifestation of a toxic effect on the spermatogonial cell population. Taking into account that in this case there is a decrease (by 40%) in the number of precursor cells for spermatogenesis, a model of testicular failure was obtained in in this study, which was caused by depletion of the sources of proliferative pool of spermatogenesis. Judging by such indices as the degree of maturity of the spermatogenic layer and the number of Sertoli cells, the control animals show features of activation of the processes of reparative regeneration of the testicular tissue. Thus, the number of microenvironment cells increases, and the degree of maturity of the spermatogenic layer decreases (Table 20). However, the functional activity of the microenvironment cells is reduced. The obtained data indicate a low regeneration potential of the spermatogenic tissue of the animals receiving Paclitaxel alone.

Forty-five days after the combined administration of Paclitaxel and Treamid (Table 20), the average number of spermatogonia increased statistically significantly in comparison with the control (Paclitaxel), the productivity of spermatogenesis did not increase statistically, but the percentage of motile sperm cells increased. An increase in the total number of spermatogonia is apparently associated with an increase in the number of committed colony-forming cells of spermatogenic tissue. In the experimental group, there was a significant increase in the average number of Sertoli cells compared to the control, but their functional activity remained reduced in the control. The degree of maturity of the spermatogenic layer did not decrease in comparison with the control values. Thus, the administration of the drug led to a decrease in the severity of pathospermia (judging by the percentage of motile forms), and an increase in the number of spermatogonia.

The study of the morphological functional state of the spermatogenic tissue of rats receiving only Paclitaxel showed that in 65 days of the experiment, the number of cells in the spermatogonial population and spermatogenesis productivity decreased (Table 21).

increase in comparison with the control, but the productivity of spermatogenesis, as judged by TNS, increased (by 43%) (see Table 21). The percentage of motile sperm forms also grew (by 32%). This index was not statistically significantly different from the background values. The number of Leydig cells was at the control level. Endocrine activity of Leydig cells normalized and reached the control values. When assessing the severity of the processes of reparative tissue regeneration, it was found that the number of Sertoli cells increased, and the degree of maturity of the spermatogenic layer was reduced. The degree of maturity of the spermatogenic layer, on the contrary, decreased significantly. These data, together with the data on an increase in the number of progenitor cells of spermatogenesis, suggest that the administration of Treamid to rats receiving Paclitaxel stimulated the processes of reparative regeneration of spermatogenic tissue. Testicular failure, judging by the percentage of motile forms, manifested itself to a lesser degree. It should be noted that the absence of a positive effect on the numbers of cells in the spermatogonial population, despite an increase in the number of progenitor cells of spermatogenesis and an increase in humoral regulation of their vital activity, clearly indicates that for the appearance of the effect on progenitor cells, a longer period of time is required. For this purpose,

TABLE 21

Assessment of spermatogenesis in rats on Day 65 after administration of Paclitaxel

| Group | The average number of spermatogonia (abs.) | The average number of Sertoli cells (abs.) | The degree of maturity of the spermatogenic layer (standard units) | Total number of sperm cells (million) | Endocrine activity of testes | Number of Leydig cells | Number of motile sperm cells (%) |
|---|---|---|---|---|---|---|---|
| Background (intact animals) | 16.95 ± 0.05 | 2.18 ± 0.06 | 6.18 ± 0.02 | 188.40 ± 8.68 | 4.33 ± 0.10 | 9.72 ± 0.19 | 85.66 ± 2.61 |
| Control (Paclitaxel) | 12.20 ± 0.19* | 1.68 ± 0.09* | 5.65 ± 0.01# | 101.40 ± 12.13* | 5.49 ± 0.33 | 9.21 ± 0.36# | 60.48 ± 2.57* |
| Experiment: Paclitaxel + Treamid | 13.07 ± 0.28* | 2.30 ± 0.03# | 5.54 ± 0.00*# | 145.20 ± 15.15*# | 4.31 ± 0.24* | 9.48 ± 0.21 | 79.81 ± 1.61* |

Note:
*differences are significant vs. background
differences are significant vs. control.

This is obviously a consequence of the above-noted depletion of the population of progenitor cells of spermatogenesis and the suppression of humoral factors that stimulate their proliferation. The percentage of motility of mature sex cells remained decreased, which indicates their partial inferiority. Thus, testicular failure caused by a decrease in the sources of the proliferative pool of spermatogenesis was detected also in this time of observation (65 days after the experiment), i.e. the experimental model of the pathological process was reproduced. The number of Leydig cells remained at the same level. The endocrine activity of Leydig cells increased. The intensity of the processes of reparative regeneration did not increase. Thus, the degree of maturity of the spermatogenic layer (although it was decreased compared to the control) did not decrease in comparison with the previous period of study, and the number of Sertoli cells also did not increase. The lack of positive dynamics during regenerative processes is obviously associated with a low number of committed colony-forming cells of spermatogenic tissue.

In animals treated with Treamid on Day 65 of the study, the number of cells in the spermatogonial population did not the morphological and functional state of spermatogenic tissue was assessed on Day 90 of the experiment.

The study of the morphological and functional state of spermatogenic tissue on Day 90 of the experiment showed that the number of cells in the spermatogonial population, TNS, and the percentage of motile forms in rats receiving Paclitaxel alone were reduced compared to these values in the control and did not increase in comparison with the previous periods of study (Table 22). These data indicate that testicular failure caused by depletion of proliferative pool sources of spermatogenesis remained. The number of Leydig cells significantly decreased, but their endocrine activity increased. The number of Sertoli cells (Table 22) did not increase and was reduced in comparison with the control. However, judging by the degree of maturity of the spermatogenic layer (this index is reduced by 10% of the background, Table 22), it is possible to speak about some activity of the processes of tissue reparative regeneration, but their intensity is clearly insufficient to restore the initial number of progenitor cells and the process of spermatogenesis as a whole.

TABLE 22

Assessment of spermatogenesis in rats on Day 90 after administration of Paclitaxel

| Group | The average number of spermatogonia (abs.) | The average number of Sertoli cells (abs.) | The degree of maturity of the spermatogenic layer (standard units) | Total number of sperm cells (million) | The average number of Leydig cells | Endocrine activity | Number of motile sperm cells (%) |
|---|---|---|---|---|---|---|---|
| Background (intact animals) | 17.25 ± 0.25 | 2.26 ± 0.04 | 6.18 ± 0.01 | 202.00 ± 7.17 | 10.49 ± 0.20 | 4.66 ± 0.09 | 77.94 ± 4.69 |
| Control (Paclitaxel) | 12.73 ± 0.09* | 1.72 ± 0.05* | 5.64 ± 0.01* | 127.70 ± 14.91* | 9.65 ± 0.19# | 5.65 ± 0.20# | 54.24 ± 6.10* |
| Experiment Paclitaxel + Treamid | 14.43 ± 0.21*# | 2.10 ± 0.06*# | 5.57 ± 0.01*# | 186.20 ± 12.74# | 9.93 ± 0.08# | 4.74 ± 4.04* | 67.80 ± 1.14*# |

Note:
*differences are significant vs. background.

In the group of animals treated with Treamid, the amount of spermatogonia was statistically elevated compared to the control, which is obviously the result of an increase in the number of the sources of proliferative pool of spermatogenesis and an increase in humoral factors that stimulate their proliferation, as was discussed above. The productivity of spermatogenesis, judging by the TNS, increased (by 46%) in comparison with the control and reached the background values. The functional activity of sperm cells also increased (the number of motile sperm cells was significantly higher than the control values). These data are evidence of the treatment effectiveness. The number of Leydig cells was similar to the control values. Their endocrine activity normalized. The intensity of the processes of reparative tissue regeneration (judging by the degree of maturity of the spermatogenic layer and the number of Sertoli cells) increased statistically significantly in comparison with the control. This is evidence that the regenerative capacity of the tissue, in the administration of the drug, remains at a high level and has not yet been exhausted.

The presented data show that Treamid allows effective stimulation of reparative regeneration of testicular tissue that was suppressed due to a decrease in the number of committed colony-forming cells. The effectiveness of Treamid is confirmed by the data of the morphological analysis of testicular tissue.

Example 8

Study of the Effect of Treamid on the Regeneration of Pancreatic Cells on the Model of Streptozotocin-Induced Pancreatic Lesion The study was performed on male C57BL/6 mice of 4 week old. Pancreatic damage was induced by intraperitoneal injection of streptozotocin at a dose of 40 mg/kg in 0.25 ml of phosphate buffer every day for 5 days [Szkudelski T. The Mechanism of Alloxan and Streptozotocin Action in B Cells of the Rat Pancreas//Physiological Research. —2001. —Vol. 50. —P. 536-546].

Treamid at a dose of 1 mg/kg was administered daily intragastrically once daily on Days 7-20 of the study.

On Days 0, 6, 10, 13, 16, 19, 21, 24, and 28 of the study, blood glucose was determined. The blood glucose level was determined after four-hour deprivation of feed with a glucometer (SencoCard glucometer, "77 Electronics Kft", Hungary).

On Day 28 of the study, the animals were euthanized in a $CO_2$ chamber, the pancreas was subjected to a morphological examination, and the pancreatic homogenate was studied on an enzyme-linked immunosorbent assay for common collagen and type I collagen.

For morphological study, a part of the pancreas adjacent to the spleen was fixed in 10% formalin and poured into paraffin. Deparaffined sections of the gland were stained with hematoxylin and eosin. On the sections, the area of 10 serial islets of Langerhans was determined by graphic computer analysis, and the total number of cells and the number of pyknotized cells were counted therein. Then, the number of cells per unit islet area and the percentage of the pyknotized cells were calculated.

Inflammatory cells (neutrophils, lymphocytes, macrophages) in the pancreatic tissue and their composition were studied by staining of the histological sections with hematoxylin-eosin and azur-eosin.

The level of mouse type I collagen in a lung homogenate was determined by enzyme-linked immunosorbent assay (Cusabio Biotech CO., LTD, China). The lung tissue homogenate was prepared according to the protocol of the manufacturer, Cusabio Biotech CO., LTD (China).

The level of the total collagen in the lung homogenate was determined by using a SIRCOL Collagen Assay kit (Biocolor Ltd, UK) for determining collagen by binding it to a dye and treating with an acid and a solution of pepsin, according to the manufacturer's instructions. The lung tissue homogenate was prepared according to the protocol of manufacturer's test system.

The results of the studies are presented in Tables 23-25.

TABLE 23

Effect of Ch-268-BH on the blood glucose level (mM/L) in C57BL/6 mice administered streptozotocin (M ± m)

| Group | Initial level | Time of study (days after the last administration of streptozotocin) | | | | | | | |
|---|---|---|---|---|---|---|---|---|---|
| | | 6 | 10 | 13 | 16 | 19 | 21 | 24 | 28 |
| Ontrol of pathology | 5.8 ± 0.4 | 11.7 ± 1.7* | 14.0 ± 1.8* | 15.0 ± 2.3* | 12.3 ± 1.9* | 13.9 ± 1.6* | 15.3 ± 1.4* | 17.2 ± 1.8* | 16.4 ± 1.7* |
| Treamid, 1 mg/kg | 5.1 ± 0.1 | 10.8 ± 0.4* | 11.2 ± 0.2* | 11.6 ± 0.3*• | 10.4 ± 1.4* | 12.0 ± 0.1* | 12.1 ± 0.4*• | 12.2 ± 1.0*• | 12.6 ± 1.1* |

Note:
*differences are significant (P < 0.05) vs. background
•differences are significant (P < 0.05) vs. pathological control

TABLE 24

Effect of Treamid on the total number of cells, the area of islets of Langerhans, and the number of pyknotized cells in the islet of Langerhans in C57Bl/6 mice administered streptozotocin, on Day 28 of the study (M ± m)

| Group | The total number of cells in the islet of Langerhans (×10$^4$) | The area of the islet tissue (pixel) | The number of piconized cells per islet (pixel) |
|---|---|---|---|
| Intact | 116.2 ± 7.55 | 695404 ± 49971 | 0.97 ± 0.11 |
| Control of pathology | 54.7 ± 5.4* | 314295 ± 30521* | 3.50 ± 0.40* |
| Treamid, 1 mg/kg | 109.9 ± 12.6• | 635770 ± 56163• | 1.75 ± 0.14• |

Note:
*differences are significant (P < 0.05) vs. intact control
•differences are significant (P < 0.05) vs. pathological control

TABLE 25

Effect of Treamid on the content of the total collagen and type I collagen in the pancreas in C57BL/6 mice with pancreatic injury, on Day 28 = of the study (M + m)

| Studied groups | Type I collagen (ng/ml) | Total collagen (mg/ml) |
|---|---|---|
| Intact | 341 ± 28 | 33 ± 36 |
| Control of pathology | 856 ± 76* | 57 ± 5* |
| Treamid, 1 mg/kg | 665 ± 55*• | 41 ± 4• |

Note:
*differences are significant (P < 0.05) vs. intact control
•differences are significant (P < 0.05) vs. pathological control The blood glucose levels were significantly increased after the administration course of streptozotocin to mice throughout the observation period (Days 6, 10, 13, 16, 19, 21, 24, 28 after the last injection of streptozotocin) (Table 23). The morphological studies made it possible to establish that edema and hyperemia were observed in the pancreatic tissue at the peak of hyperglycemia (Days 21, 28): pancreatic infiltration with neutrophils, macrophages and lymphocytes was recorded. In addition, starting from Day 6 after the last injection of streptozotocin, the mice of the experimental group demonstrated an increasing decrease in the area of islet tissue in comparison with the intact control. On Day 28, the decline of this parameter was most pronounced: the total cellularity of the islet was reduced by more than 50% compared to the intact mice, the percentage of pyknotized cells, by contrast, increased significantly (by 2.3 times), and in the injured islets there were appeared fibroblasts, which was indicative of the development of the insular apparatus sclerosis (Table 24). Immunoenzymatic analysis of pancreatic homogenates in the pathological control group revealed an increase in the levels of type I collagen and the total collagen in comparison with the intact animals on Day 28 of the study (Table 25).

The administration of Treamid at a dose of 1 mg/kg significantly reduced the blood glucose level in mice received streptozotocin on Days 13, 21, and 24 of the study (Table 1). Morphological examination of the pancreas performed on Day 28 of the study showed that Treamid reduced the number of pyknotized pancreatocytes in the islets of Langerhans in sick animals, increased the area and cellularity of the islet tissue (Table 24), reduced the concentration of the total collagen and type I collagen in the pancreas in the experimental animals compared to the pathological control (Table 25).

The obtained results allow the conclusion that on the model of streptozotocin-induced pancreatic lesion, Treamid exerts a regenerative action on the pancreatic tissue. As a result, the number of cells in the islets of Langerhans is restored, the area of the islet tissue increases, the number of pyknotized cells in the islet of Langerhans is normalized, the fibrotic changes in pancreatic tissue decrease, and as a result the blood glucose level decreases. Treamid can be used in the treatment of impaired glucose tolerance.

Example 9

Study of the Effect of Treamid on the Regeneration of Pancreatic Cells and Recovery of the Function of Testicular Tissue in Male Mice on a Metabolic Syndrome Model Metabolic disorders were simulated as follows: on Day 2 after birth, male C57Bl/6 mice were injected with streptozotocin at a dose of 200 mg/kg once, subcutaneously in the withers area, and the volume of the injected solution was 30 µl. From week 4 after birth, the animals were transferred to a diet high in fat. For this purpose, the used feed was enriched with heavy saturated fats (30% fat) (Siff EF R/M with 30% Fat Cat No. E15116-34, Germany). The duration of feeding with a high-fat feed was 42 days (from Day 28 to Day 70 of the experiment). Treamid was administered at a dose of 10 mg/kg intragastrically once daily, every day from Day 49 to Day 70 of the experiment. The control animals received the equivalent volume of a solvent (2% starch mucus), instead of the test compound.

On Days 28, 35, 42, 49, 56, 63, and 70 of the study, blood glucose was determined. The blood glucose level was determined with a glucometer meter (Accu-Chek Performs Nanu ("Roche Diagnostes GmbH", Germany). Blood glucose was measured in animals after 16-hour feed deprivation; all subsequent measurements of the glucose level were also performed after 16-hour feed deprivation.

On Day 70 day, animals were euthanized in a $CO_2$ chamber. Then, the serum free testosterone level was studied, and the morphological examination of the pancreas was performed.

The level of free testosterone in the serum was evaluated by enzyme immunoassay according to the protocol of manufacturer's test system.

For morphological study, a part of the pancreas adjacent to the spleen was fixed in 10% formalin and poured into paraffin according to the standard method.

Deparaffined sections of the gland were stained with hematoxylin and eosin. On the sections, the area of 10 serial islets of Langerhans was determined by graphic computer analysis, and the total number of cells and the number of pyknotized cells were counted therein. Then, the number of cells per unit islet area and the percentage of the pyknotized cells were calculated. Inflammatory cells (neutrophils, lymphocytes, macrophages) in the pancreatic tissue and their composition were studied by staining of the histological sections with hematoxylin-eosin.

Figure 1:
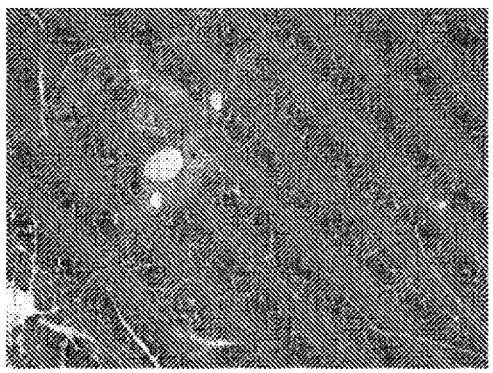
FIG. 1 is a morphological pattern of pancreas in male C57Bl/6 mice of intact control, on Day 70 of untreated metabolic disorders (pathological control) and on Day 70 of metabolic disorders treated with the Treamid at a dose of 10 mg/kg. Staining with hematoxylin and eosin.
Figure 1:
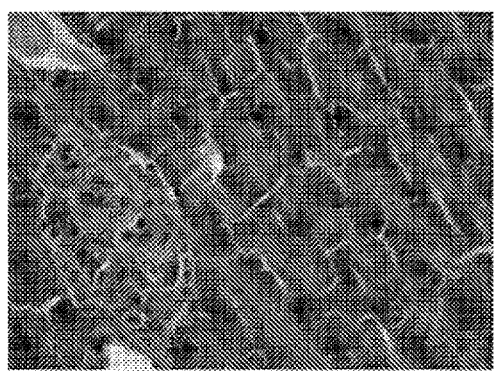
Figure 1:
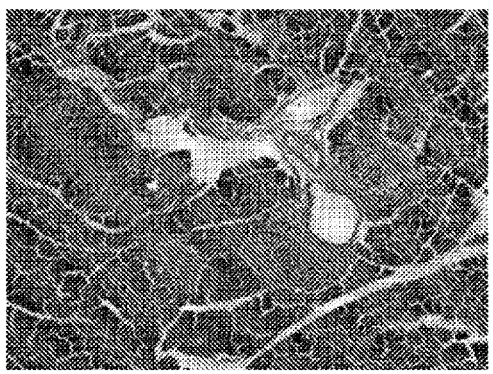
Figure 1:
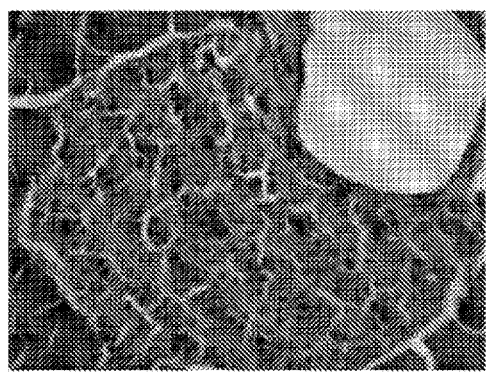
Figure 1:
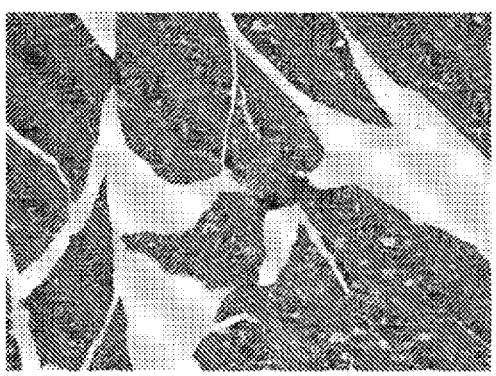
Figure 1:
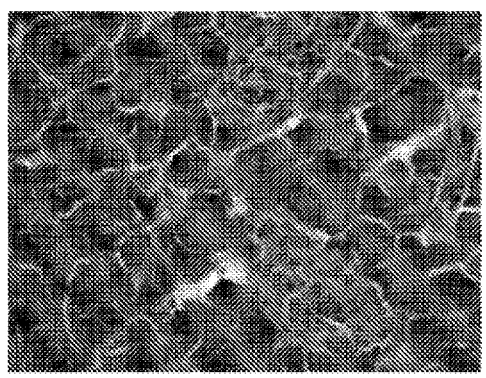

The results of the study showed that the simulation of the metabolic syndrome caused edema and hyperemia in the pancreatic tissue in C57Bl/6 male mice on Day 70 of the experiment (FIG. 1). In addition, mice under the model conditions had registered small and medium-droplet fatty degeneration of acinar cells, thickening and proliferation of interlobular septa, infiltration of islet tissue by inflammation cells, a decrease in the total number of islets of Langerhans, a decrease in their area and cellularity, as compared with those in the animals of the intact control; however, the percentage of pyknotized cells in the islets increased (FIG. 2, Table 26).

Intragastric administration of Treamid at a dose of 10 mg/kg from Day 49 to Day 70 of the study prevented destruction of the pancreas in mice with the simulated metabolic disorders. Treamid increased the number of islets of Langerhans in the pancreas and their cellularity, prevented the development of fatty degeneration of acinar cells, and significantly reduced the number of pyknotized cells in the islets of Langerhans in the mice with metabolic disorders. In addition, Treamid reduced the intensity of edema and infiltration of the islet tissue by inflammation cells (FIGS. 1 and 2, Table 26).

TABLE 26

Morphology of the pancreas of mice on Day 70 of the simulation of metabolic disorders (M ± m)

| Group | The number of islets in 30 vision fields | % of pyknotized cells in the islet of Langerhans | The number of cells in the islet of Langerhans | Area of an islet (pixel) |
|---|---|---|---|---|
| Intact (n = 10) | 7.0 ± 0.42 | 1.11 ± 0.06 | 152.8 ± 3.6 | 1240813 ± 48607 |
| Control (n = 10) | 3.3 ± 0.26* | 3.17 ± 0.24* | 72.3 ± 1.4* | 596043 ± 9924* |
| Treamid (1 mg/kg) (n = 8) | 7.4 ± 0.37• | 0.99 ± 0.06• | 101.8 ± 3.0*• | 743399 ± 21134*• |

Notes:
1 - # - differences are significant vs. background (p < 0.05, Mann-Whitney U-test),
2 - # - differences are significant vs. control (p < 0.05, Mann-Whitney U-test).

The results of the study of glucose in the blood serum of mice showed that the simulation of metabolic disorders led to a persistent increase in the blood glucose levels in male C57BL/6 mice, starting from Day 42 of the experiment. A high glucose level persisted for up to 70 days. The maximum values of the index were registered on Day 63 of the experiment and exceeded the baseline by 3.8 times, and on Day 70-4.2 times (Table 27).

Intragastric administration of Treamid at a dose of 10 mg/kg from Day 49 to Day 70 of the experiment reduced the level of glucose in the blood of mice on Days 56 and 63 (Table 27).

Thus, the course of administration of Treamid at a dose of 10 mg/kg caused hypoglycemic effects in male C57BL/6 mice with simulated metabolic disorders.

TABLE 27

Serum glucose concentration (mmol/L) of mice under the conditions of simulation of metabolic disorders and the use of Treamid at a dose of 10 mg/kg (M ± m)

| Time of analysis | Intact (n = 10) | Pathological control (n = 10) | Treamid, 10 mg/kg (n = 8) |
|---|---|---|---|
| Day 28 | 4.72 ± 0.81 | 6.02 ± 2.02 | 5.36 ± 1.28* |
| Day 35 | 4.6 ± 0.87 | 4.74 ± 1.87 | 4.21 ± 1.81* |
| Day 42 | 4.91 ± 0.96 | 10.84 ± 1.97* | 12.75 ± 2.6* |
| Day 49 | 5.33 ± 0.89 | 10.47 ± 1.96* | 13.59 ± 2.41* |
| Day 56 | 5.07 ± 0.86 | 19.58 ± 6.34* | 12.91 ± 4.48*• |
| Day 63 | 5.43 ± 0.81 | 20.51 ± 3.85* | 14.47 ± 3.21*• |
| Day 70 | 4.64 ± 0.92 | 19.77 ± 4.99* | 21.82 ± 5.83* |

Notes:
1 - # - differences are significant vs. background (p < 0.05, Mann-Whitney U-test),
2 - # - the differences are significant vs. control (p < 0.05, Mann-Whitney U-test).

The results of the study of free testosterone in the mouse blood serum showed a decrease (by 1.6 times) in the hormone content in the males of the pathological control group in comparison with the intact animals. The obtained data indicate the formation of hypogonadism in the laboratory males with metabolic disorders, which reproduces the clinical picture in humans.

The course of administration of Treamid at a dose of 10 mg/kg restored the concentration of free testosterone in the blood to the level of the intact animals (Table 28). Thus, the studied pharmaceutical substance prevented the development of hypogonadism induced by metabolic disorders.

TABLE 28

Serum level of free testosterone in mice on Day 70 of simulation of metabolic disorders (M ± m)

| Group | Free testosterone (pg/ml) |
|---|---|
| Intact (n = 10) | 3.06 ± 0.49 |
| Pathological control (n = 10) | 1.97 ± 0.31* |
| Treamid, 10 mg/kg (n = 8) | 3.70 ± 0.46• |

Notes:
1 - # - differences are significant vs. background (p < 0.05, Mann-Whitney U-test),
2 - # - differences are significant vs. control (p < 0.05, Mann-Whitney U-test).

The obtained results allow the conclusion that on the model of metabolic syndrome in male mice, Treamid exerts a regenerative action on the pancreatic tissue. As a result, the number of cells in the islets of Langerhans is restored, the area of the islet tissue increases, the number of pyknotized cells in the islet of Langerhans is normalized, the fibrotic changes in pancreatic tissue decrease, and as a result the blood glucose level decreases. Treamid also restores the function of the testicular tissue, preventing the development of hypogonadism. Thus, Treamid can be used in the treatment of metabolic syndrome and hypogonadism.

Example 10

Study of the Effect of Treamid on the Regeneration of Pancreatic Cells and Restoration of the Function of Testicular Tissue in Male Rats on a Metabolic Syndrome Model Metabolic syndrome was simulated in male Wistar rats (260-280 g) by keeping animals on a high-fat diet ("cafeteria diet") for 12 weeks. The "cafeteria diet" was balanced according to Current Protocols in Pharmacology [Current Protocols in Pharmacology (2005) Animal Models of Disease//Contributed by Petter Hedlund, Kenshi Matsumoto, and Karl-Erik Andersson]. The diet contained 25-35% of fats and 25-30% of digestible carbohydrates in addition to the standard diet of rodents. Treamid was administered at a dose of 0.5 mg/kg intragastrically once daily, every day from Week 7 to Week 11 of the diet. Reference drug Metformin was administered at a dose of 200 mg/kg intragastrically according to the same regimen.

The development of pathology and a therapeutic effect of Treamid were estimated by the following parameters: blood biochemical parameters (glucose, cholesterol, triglycerides (TG), HDL, LDL, atherogenicity index), glucose tolerance test, visceral fat weight, total number and percentage of motile sperm forms.

Glucose was determined with an OneNouch Select glucometer (Switzerland).

The levels of triglycerides, TCh and HDL were determined by using a diagnostic kit (Olvex Diagnosticum, Russia).

The level of LDL was determined by the formula 2.

$$LDL=TCh-(HDL+TG/2.2) \quad (1),$$

where LDL is a low-density lipoprotein cholesterol;
HDL is high-density lipoprotein cholesterol;
TCh is total cholesterol;
TG is triglycerides.

The atherogenicity index (AI) was calculated by the formula 3.

$$AI=(TCh-HDL)/HDL \quad (2),$$

where AI is the atherogenicity index;
HDL is high-density lipoprotein cholesterol.

The atherogenicity index was calculated for each animal individually, and then the arithmetic mean value of the group was calculated.

For the analysis of sperm, the animals were anesthetized with intraperitoneal injection of a mixture of Zolletil and Xyla (0.2 ml of Zoletil+0.8 ml Xyla) in a volume of 70 µl/100 g of weight. Epididymis was isolated. The epididymis head was cut off from the tail, weighed, 5 incisions were made (to improve the sperm yield), and placed in a tube containing 10 ml of phosphate buffered saline heated to 37° C. The tube was held at 37° C. for 10 minutes. Then, the tube was shaken on a shaker, 20 µl of the liquid was taken, applied to a glass slide heated to 37° C., and the number of motile sperm cells was assessed under a microscope. The calculation was performed up to 100 sperm cells.

The total number of sperm cells in a test tube with epididymis was calculated as follows: 20 µl of the liquid was taken after shaking and added to a tube containing 400 µl of physiological saline. After shaking the tubes, their contents (20 µl) were taken out and introduced into Goryaev chamber. The number of sperm cells was counted in 100 large squares. The number of sperm cells in the head of epididymis was calculated by the formula:

Number of sperm cells=number of sperm cells in 100 large squares of Goryaev chamber*0.525 (factor from the calculation of the dilution and the volume of Goryaev chamber)/weight of the epididymis head.

The results of the study are presented in Tables 29-32.

The measurement of visceral fat weight in experimental animals showed that in receiving a high fat diet, the visceral fat near the kidneys, intestines and testes grows evenly: by 1.7, 1.5 and 2.0 times, respectively (Table 29). The total weight of visceral fat in the control group increased by approximately 1.7 times compared with the intact animals. The obtained results gave grounds to conclude that in the experimental animals held on the high-fat diet, abdominal obesity developed, which is one of the symptoms of metabolic syndrome.

The administration of Treamid (0.5 mg/kg dose) to male rats reduced the visceral fat weight gain by 1.3 times in comparison with the control group. Metformin had a similar effect (Table 29).

TABLE 29

Relative weight of visceral fat, % based on body weight (M ± m, n = 8)

| Group | Fat near the kidneys | Fat near the intestine | Fat near the testes | Total fat |
|---|---|---|---|---|
| Intact | 0.49 ± 0.06 | 0.80 ± 0.09 | 0.64 ± 0.08 | 1.94 ± 0.15 |
| Control | 0.81 ± 0.1* | 1.20 ± 0.15* | 1.29 ± 0.19* | 3.30 ± 0.27* |
| Treamid (0.5 mg/kg) | 0.48 ± 0.05& | 0.94 ± 0.07 | 1.03 ± 0.14* | 2.46 ± 0.15*& |
| Metformin (200 mg/kg) | 0.52 ± 0.05& | 1.07 ± 0.08* | 0.98 ± 0.12* | 2.57 ± 0.18*& |

Note:
*differences are statistically significant vs. intact animals (p < 0.05);
&differences are statistically significant vs. control (p < 0.05)

Results of the glucose measurement (fasting) in whole blood of rats are given in Table 30. The first measurement was made prior to the administration of the drugs to animals on Week 6 of the study. Table 30 shows that in the intact rats on the standard diet, the glucose level on Week 6 of the diet was 3.9±0.3 mmol/l, and 6.8±0.93 mmol/l on Week 12 of the diet. In turn, in rats held on the high-fat diet, the glucose level on Week 6 of the diet was 6.7±0.3 mmol/l, and 11.6±0.9 mmol/l on Week 12 of the diet. Thus, in animals receiving the high-fat diet had a pronounced hyperglycemia, which is another symptom of metabolic syndrome.

Intragastric administration of Treamid to the experimental animals, starting from Week 7 of the high-fat diet, inhibited an increase in the glucose level in the blood. The effect of Treamid appeared 3 weeks after the therapy and retained until the end of the study (Table 30).

TABLE 30

Dynamics of the glucose level in the blood of male rats, mmol/l

| Group | Glucose level in the blood of male rats, mmol/L | | | |
|---|---|---|---|---|
| | before administration of drugs | 3 weeks after the drug administration | 5 weeks after the drug administration | one week after the drug withdrawal |
| Intact | 3.9 ± 0.3 | 3.7 ± 0.2 | 4.5 ± 0.2 | 6.8 ± 0.9 |
| Control | 6.7 ± 0.3* | 8.7 ± 0.4* | 9.1 ± 0.4* | 11.6 ± 0.9* |
| Treamid (0.5 mg/kg) | 6.4 ± 0.2* | 6.5 ± 0.2*& | 7.8 ± 0.2*& | 8.3 ± 0.7& |
| Metformin (200 mg/kg) | 6.2 ± 0.1* | 6.9 ± 0.3*& | 8.0 ± 0.2*& | 7.8 ± 0.6& |

Notes:
1 - *differences are statistically significant vs. intact animals ($p < 1$);
2 - &differences are statistically significant vs. control ($p < 2$).

The effect of Treamid on lipid metabolism was estimated by measuring TCh, TG, LDL, HDL, and atherogenicity index on Week 12 of the study.

The use of the "cafeteria diet" in animals led to a marked statistically significant increase in the level of total cholesterol, TG, LDL and to a decrease in the level of HDL compared to intact animals (Table 31). The calculated index, atherogenic index, in animals of the control group was 4.2 times higher than that in the intact animals. Intragastric administration of Treamid increased the level of HDL from 1.5±0.2 to 1.9±0.2 and decreased the atherogenicity index from 2.1±0.4 to 0.9±0.2. This gives grounds to conclude that the long-term administration of Trehamide provides its anti-atherogenic effect (Table 31).

TABLE 31

Lipid spectrum of the blood of male rats held on the high-fat diet for 12 weeks (M ± m, n = 8)

| Estimated index | Intact (standard diet) | Control (high-fat diet) | Treamid (0.5 mg/kg) | Metformin (200 mg/kg) |
|---|---|---|---|---|
| Total cholesterol, mM/l | 2.6 ± 0.1 | 3.3 ± 0.2* | 3.5 ± 0.1* | 2.8 ± 0.3 |
| HDL, mM/l | 1.7 ± 0 | 1.1 ± 0.1* | 1.9 ± 0.2& | 1.8 ± 0& |
| LDL, mM/l | 0.5 ± 0.1 | 1.6 ± 0.3* | 1.2 ± 0.2* | 0.7 ± 0.3& |
| Atherogenicity index | 0.5 ± 0.04 | 2.1 ± 0.4* | 0.9 ± 0.2*& | 0.6 ± 0.1& |
| Triglycerides, mM/l | 0.7 ± 0 | 1.1 ± 0.0* | 0.9 ± 0.1* | 0.7 ± 0.1& |

Note:
*differences are statistically significant vs. intact animals ($p < 0.05$);
&differences are statistically significant vs. control ($p < 0.05$)

Table 31 shows that in the group receiving the "cafeteria diet", the total number of sperm cells and the percentage of motile sperm forms were 2 times lower than in animals held on the standard diet. This corresponds to the clinical data on deterioration in sperm quality in men with metabolic disorders. Intragastric administration of Treamid increased the total number of sperm cells by 1.7 times and the percentage of motile sperm forms by 1.5 times, bringing these indices to the level of the intact animals. Thus, it can be concluded that Treamid not only has a therapeutic effect on the main symptoms of metabolic syndrome, but also restores the quality of sperm deteriorated by existing pathology.

Metformin therapy also increased the total number of sperm cells by 1.8 times, but unlike Treamid did not affect the percentage of motile sperm forms (Table 32).

TABLE 32

The total number of sperm cells and the percentage of motile sperm forms in male rats on the model of a metabolic syndrome induced by a high fat diet (M ± m, n = 8)

| Group | Total number of sperm cells | Percentage of motile sperm forms |
|---|---|---|
| Intact (standard diet) | 304.2 ± 46.2 | 42.43 ± 4.09 |
| Control (high-fat diet) | 154.5 ± 17.6* | 22.71 ± 3.13* |
| Treamid (0.5 mg/kg) | 260.0 ± 38.7& | 34.43 ± 3.15& |
| Metformin (200 mg/kg) | 276.6 ± 44.6& | 24.43 ± 3.99* |

Note:
*differences are statistically significant vs. intact animals ($p < 0.05$);
&differences are statistically significant vs. control ($p < 0.05$)

Thus, in the male metabolic syndrome, Treamid reduced an increase in the blood glucose, reduced the atherogenic index, reduced the amount of visceral fat increased in the presence of pathology, and restored the total number of sperm cells and the percentage of their motile forms reduced due to endocrine disorders. This confirms the ability of Treamid to restore the function of the pancreas and testicular tissue. Treamid is recommended for administration in metabolic syndrome and reduced function of testicular tissue.

Example 11

Study of the Effect of Treamid on the Fertility of Male Mice on a Metabolic Syndrome Model Metabolic disorders were simulated as follows: on Day 2 after birth, male C57Bl/6 mice were injected with streptozotocin at a dose of 200 mg/kg, once, subcutaneously in the withers area, and the volume of the injected solution was 30

μl. From week 4 after birth, the animals were transferred to a high-fat diet. For this purpose, the used feed was enriched with heavy saturated fats (30% fat) (Siff EF R/M with 30% Fat Cat No. E15116-34, Germany). The animals were held on the high-fat diet for 42 days (from Day 28 to Day 70 of the study). Treamid was administered at a dose of 10 mg/kg intragastrically once daily, every day from Day 49 to Day 80 of the experiment. The control animals received the equivalent volume of a solvent, instead of the test compound.

The fertility of the males was estimated as follows: intact females were placed to the males of the experimental groups in a ratio of 1:2 for a period of from Day 70 to Day 80 of the study. During this period, the males of the experimental group continued to be administered intragastrically Treamid once daily at a dose of 10 mg/kg.

At the end of the mating period, on Day 80 of the study, the males were euthanized in a $CO_2$ chamber. The blood of the animals was taken and analyzed for serum levels of free testosterone by enzyme immunoassay. Euthanasia was performed in the morning hours from 9:30 to 11:00.

The females were sacrificed in the $CO_2$ chamber on Day 18 of pregnancy. The fetuses in the uterus were examined. The fertility index (FI) was calculated to assess fertility: FI=number of fertilized females/number of females placed with males×100%.

The results of the study of free testosterone in blood serum in males of C57Bl/6 mice after simulation of metabolic disorders and administration of Treamid at a dose of 10 mg/kg, on Day 80 of the experiment are presented in Table 33. The simulation of metabolic disorders caused a decrease in the concentration of free testosterone in the blood serum on Day 80 of the experiment by 1.8 times in comparison with the group of intact animals (Table 33).

The course administration of Tremide at a dose of 10 mg/kg increased the level of free testosterone in the blood serum of mice with metabolic disorders by 2 times in comparison with the pathological control and by 16% in comparison with intact animals.

Thus, Treamid at a dose of 10 mg/kg restored the level of free testosterone in the blood serum in mice with metabolic disorders.

TABLE 33

The content of free testosterone in the blood serum of mice with hypogonadism caused by metabolic disorders (M ± m, n = 10)

| Group | Free testosterone in the blood serum (pg/ml) |
|---|---|
| Intact | 2.99 ± 1.89 |
| Pathological control | 1.66 ± 0.43* |
| Treamid (10 mg/kg) | 3.46 ± 1.87*• |

Notes:
1 - # - differences are significant vs. background (p < 0.05, Mann-Whitney U-test),
2 - # - differences are significant vs. control (p < 0.05, Mann-Whitney U-test).

The results of the study of the fertility of mice on Days 70-80 after the simulation of metabolic disorders and the administration of Treamid at a dose of 10 mg/kg are presented in Table 34.

It was found that the fertility index of males with metabolic disorders on Days 70-80 of the study was reduced by 2.8 times as compared with the intact control. In males with metabolic disorders receiving Treamid at a dose of 10 mg/kg from Day 49 to Day 80, the fertility index was 1.8 times higher than in males with untreated metabolic disorders (pathological control) (Table 34).

TABLE 34

Fertility index of male mice under the conditions of simulation of metabolic disorders and the administration of Treamid at a dose of 10 mg/kg (n = 20)

| Group | Fertility index, % |
|---|---|
| Intact control | 85 |
| Pathological control | 30* |
| Treamid (10 mg/kg) | 55*• |

Notes:
*differences are significant vs. background (p < 0.05, according to Fisher's test);
•differences are significant vs. control (p < 0.05, according to Fisher's test).

Thus, on the metabolic syndrome model, Treamid effectively restored the function of the testicular tissue of male mice, which led to an increase in the fertility of animals. Treamid is recommended for the treatment of metabolic syndrome, hypogonadism and male infertility.

Example 12

Study of the Effect of Treamid on the Recovery of Liver Tissue on a Chronic Toxic Hepatitis Model Chronic toxic hepatitis was induced in the male CBA/CaLac mice by intragastric administration of a 20% carbon tetrachloride ($CCl_4$) solution in olive oil in a volume of 0.2 ml/mouse on Days 0, 3, 7, 10, 14, and 17 of the study. Treamid was administered at a dose of 10 mg/kg intragastrically once daily, every day from Day 14 to Day 27 of the study. On day 28, the animals were euthanized in a $CO_2$ chamber and a liver biopsy sample was taken for histological analysis.

For histological examination, the liver was fixed in a 10% neutral formalin solution and then poured into paraffin by the standard method. Deparaffined sections of a thickness of 5 μm were stained: 1) with hematoxylin and eosin according to the standard procedure for routine histological examination; and 2) with picrofuxin for the calculation of the area of connective tissue, using a graphic data processing software.

The results of the study showed that 2 weeks after the last injection of $CCl_4$, morphological changes specific for toxic hepatitis were registered in the liver of mice. Thus, preparations stained with hematoxylin and eosin showed small and medium-droplet fatty degeneration, monocellular and bridge-like necrosis of hepatocytes, as well as the development of infiltration by the cells of inflammation (mainly macrophages and lymphocytes) of hepatic parenchyma with a different extent of severity (FIG. 3). In addition, the beam structure of the liver was broken due to edema and venous plethora. The latter indicates hemodynamic disorders in the liver of mice administered $CCl_4$.

The staining of the liver preparations with picrofuxin allowed registration of an increase in the content of connective tissue in periportal zones and the proliferation of septal collagen from portal spaces, in animals with toxic hepatitis (FIG. 3).

Intragastric administration of Treamid to animals at a dose of 10 mg/kg significantly reduced the severity of infiltration by cells of inflammation of the diseased liver, reduced the amount of monocellular necrosis and the intensity of fatty degeneration, markedly reduced the content of connective tissue in the liver of sick animals, compared to the pathological control. The histological pattern of the liver of the treated animals on Day 28 of the experiment did not differ from that of the intact control (FIG. 3).

Thus, on the chronic toxic hepatitis model, Treamid had a regenerative effect on the liver tissue: reduced fibrosis, reduced the intensity of fatty degeneration, and prevented the development of necrosis. This allows the conclusion that Treamid can be used as a drug that restores the structural and functional characteristics of liver tissue.

Example 13

Study of the Effect of Treamid on the Recovery of Lung Tissue on a Pulmonary Emphysema Model Pulmonary emphysema was induced in female C57Bl/6 mice by a single intratracheal administration of elastase (Sigma, USA) at a dose of 0.6 U/mouse in 30 µl of 0.9% NaCl [Luthje L., Raupach T., Michels H. et al.//Respiratory Research 2009, 10: 7]. The day of operation was taken as Day 0 of the experiment. Treamid was administered at a dose of 10 mg/kg intragastrically once daily, every day from Day 7 to Day 60 of the study. On Days 7, 14, 30 and 60, the animals were euthanized in a $CO_2$ chamber, and their lungs were isolated.

The dynamics and severity of the developed emphysema in the lung tissue were assessed on histological preparations. For this, the lungs were fixed in a 10% neutral formalin solution and then poured into paraffin by the standard method. The preparations of the lung apex, middle lung field, and lower lung field of a thickness of 5 µm were prepared from the deparaffined sections, and stained with hematoxylin and eosin by the standard procedure. Further, photographs of the lung apex, middle lung field, and lower lung field were made, and the localization and area of emphysema were studied by using graphics processing software. The area of emphysematously enlarged lung tissue (% of normal tissue) was measured as an estimated score of the development of emphysema, and blood vessels and bronchi were excluded from the calculations [ArrateMunoz-Barrutia, Mario Ceresa, Xabier Artaechevarria, Luis M. Montuenga, and Carlos Ortiz-de-Solorzano. Quantification of Lung Damage in an Elastase-Induced Mouse Model of Emphysema//International Journal of Biomedical Imaging. Volume 2012, Article ID 734734, pages; Susumu Sato, Erzsébet Bartolák-Suki, Harikrishnan Parameswaran, Hiroshi Hamakawa1 and Béla Suki. Scale dependence of structure-function relationship in the emphysematous mouse lung//Front. Physiol. 6:146. doi: 10.3389/fphys.2015.00146].

The experiments showed that the elastase thinned the walls of the alveoli and bronchioles, significantly enlarged the lumen area, and on Day 7 caused ruptures of the alveolar walls (Table 13). The mucous membrane of the bronchi and bronchioles had a scalloped outline and was lined with a cylindrical and cubic (in bronchioles) respiratory-type epithelium, and there were moderate desquamative changes. Additionally, histological preparations of the lungs showed moderate hyperemia of the capillaries of interalveolar septa and a microcirculation disturbance: there was a moderate plethora of the vessels of the microcirculatory bed and capillaries of interalveolar septa in the lungs.

TABLE 35

The area of emphysematously enlarged lung tissue (% of normal) in female C57Bl/6 mice receiving intratracheally elastase (M ± m, n = 10).

| Group | Lung apex | Middle lung field | Lower lung field |
|---|---|---|---|
| Intact control | 0 | 0 | 0 |
| Day 7 of the experiment | | | |
| Pulmonary emphysema | 1.3 ± 0.03* | 6.5 ± 0.98* | 43.0 ± 5.85* |
| Pulmonary emphysema treated with Treamid (10 mg/kg) | 0.9 ± 0.12*• | 5.4 ± 0.55* | 41.3 ± 1.82* |
| Day 14 of the experiment | | | |
| Pulmonary emphysema | 1.9 ± 0.06* | 34.1 ± 4.42* | 53.6 ± 6.57* |
| Pulmonary emphysema treated with Treamid (10 mg/kg) | 0.7 ± 0.09*• | 29.03 ± 1.76* | 42.6 ± 1.79*• |
| Day 30 of the experiment | | | |
| Pulmonary emphysema | 11.8 ± 1.83* | 26.2 ± 1.84* | 68.2 ± 7.61* |
| Pulmonary emphysema treated with Treamid (10 mg/kg) | 2.4 ± 1.6*• | 18.5 ± 2.91* | 32.8 ± 3.78*• |
| Day 60 of the experiment | | | |
| Pulmonary emphysema | 7.7 ± 0.68* | 23.8 ± 2.51* | 56.9 ± 6.41* |
| Pulmonary emphysema treated with Treamid (10 mg/kg) | 3.6 ± 0.26*• | 24.9 ± 3.11* | 40.0 ± 3.57*• |

Notes:
*differences are significant vs. intact control (P < 0.05);
•differences are significant vs. pathological control (P < 0.05).

A significant part of the elastase lung tissue was occupied by emphysematously enlarged alveoli with destroyed interalveolar septa. The area of emphysematously enlarged tissue in the lower lung field reached 43% of the area of normal lungs, 6.5% in the middle lung field, and 1.3% in the lung apex. As can be seen emphysema was localized mainly in the lower lung field. In addition to the expansion of the alveoli, there were ruptures of the alveolar septa. Emphysematously enlarged alveoli caused compression of unchanged alveoli, resulting in focal atelectasis in the lungs. On Day 7, the connective tissue area in elastase lungs decreased more than 3 times (P<0.05) compared to the intact control. In addition, it was noted that elastase led to thickening of the alveolar walls due to lympho-macrophage infiltration and inflammatory infiltration of the interstitial tissue. The lumen of individual alveoli was also filled with macrophages and lymphocytes (Table 35).

On Day 14, the progression of emphysema was observed: an increase in the area of emphysematously enlarged alveoli in the middle and lower lung fields reached 34.1% and 53.6%, respectively, and their walls were thinned (Table 35, FIG. 4). This led to the thinning of the alveolar capillaries and their desolation. To Day 30 of the observation, the percentage of emphysematously enlarged tissue in the lung apex and in the lower lung field increased. On Day 60, the value of the index was slightly lower compared to that in Day 30.

Administration of Treamid to mice caused a decrease in the intensity of inflammatory infiltration of the lung parenchyma throughout the observation period. The drug reduced the area of the emmphysematously enlarged alveoli in the lung apex (Days 7, 14, 30, and 60) and in the lower lung field (Days 14, 30, and 60) compared to the pathological control group (Table 35, FIG. 4).

Thus, oral administration of Treamid had a regenerative effect on the lung tissue on the elastase-induced pulmonary emphysema model: a decrease in the area of emphysematously enlarged lung tissue was registered. This allows the conclusion that Treamid can be used as a drug that restores the structural and functional characteristics of lung tissue.

Example 14

Study of the Effect of Treamid on the Development of Pulmonary Fibrosis

Toxic damage of the lung alveolar epithelium causing pulmonary fibrosis was simulated by intra-tracheal administration of the cytostatic bleomycin once in a dose of 80 µg/mouse in 30 µl of physiological saline. Anesthesia during the operation was achieved by using inhalation ether. The surgical field was disinfected with a 70% ethanol solution and hair on this field was removed. The skin, subcutaneous tissue and own fascia of the neck were dissected along the middle line of the neck. The muscles were moved apart on the ventral side of the trachea by the method of blunt separation of tissues. Injection of bleomycin was made on inhalation along the airflow by a Hamilton syringe. After suturing the wound, the surgical field was treated with an antiseptic. The administration of bleomycin was taken as Day 0 of the experiment.

The effectiveness of Treamid and the reproduction of pulmonary fibrosis were estimated by the number and intensity of the synthesis of connective tissue in the lungs, as well as by the histoarchitectonics of the lungs.

The conducted experiments showed that changes in the morphological pattern of the lungs of male C57BL/6 mice after a single intratracheal administration of bleomycin were similar to the changes that are specific to pulmonary fibrosis. Thus, the staining of histological preparations of the lungs of C57BL/6 mice with picrofuxin according to Van Gieson and subsequent visualization of the connective tissue made it possible to register a significant proliferation of the connective tissue, mainly around the vessels and bronchioles (FIG. 5, Table 36). In addition, lung homogenates of the animals of the intact control and pathological control were investigated by enzyme immunoassay. As can be seen from Table 37, intratracheal administration of bleomycin significantly increased the levels of type I collagen, total collagen, and hydroxyproline.

TABLE 36

The content of connective tissue (%) in the lungs in C57Bl/6 mice with pulmonary fibrosis on Day 21 of the experiment (M ± m, n = 10)

| Intact control | Pulmonary fibrosis (Pathological control) | Pulmonary fibrosis, treated with Ch-268-BG at a dose of 10 mg/kg |
|---|---|---|
| 0.91 ± 0.09 | 2.29 ± 0.13* | 1.17 ± 0.20• |

Notes:
*differences are significant vs. intact control (P < 0.05);
•differences are significant vs. pathological control (P < 0.05).

TABLE 37

The level of the total collagen, type I collagen, and hydroxyproline in the lungs in C57Bl/6 mice with pulmonary fibrosis on Day 21 of the experiment (M ± m, n = 10)

| | Studied groups | | |
|---|---|---|---|
| | Type I collagen (ng/ml) | Total collagen (mg/ml) | Hydroxyproline (µg/ml) |
| Intact control | 204 ± 17 | 22.3 ± 1.5 | 26.12 ± 2.3 |
| Pulmonary fibrosis (pathological control) | 248.4 ± 21* | 32.6 ± 2.2* | 39.01 ± 2.6* |
| Pulmonary fibrosis, treated with Ch-268-BG at a dose of 10 mg/kg | 201.6 ± 18• | 23.4 ± 1.7• | 27.97 ± 2.2• |

Notes:
*differences are significant vs. intact control (P < 0.05);
•differences are significant vs. he pathological control (P < 0.05).

Treamid at a dose of 10 mg/kg was effective in the treatment of pulmonary fibrosis: the amount of deposited collagen fibers around the vessels and bronchioles was reduced to the level of the intact control (FIG. 5, Table 37). An additional characteristic of the antifibrotic effect of Treamid was a significant drop in the concentration of collagen, type I collagen, and hydroxyproline in the lung homogenates of mice with pulmonary fibrosis (Table 37).

The obtained results allow the conclusion that in pulmonary fibrosis, Treamid has an antifibrotic effect that is manifested in the normalization of the production of fibroblasts by collagen fibers. This indicates the ability of Treamid to regenerate fibroblasts of lung tissue. Thus, Treamid can be used as a drug that prevents the development of lung fibrosis and contributes to the regeneration of the lung tissue.

Example 15

Study of the Effect of Treamid on the Development of Cachexia in Animals with a Tumor Cachexia developed in male C57Bl/6 mice when simulating hematogenously metastasizing Lewis lung carcinoma (LLC). Tumor cells were injected once subcutaneously into the mice at a concentration of $5 \times 10^6$ in 0.1 ml of physiological saline (Yu-Chou T., Samuel K. K., I-Lu L. et al. Preclinical Investigation of the Novel Histone Deacetylase Inhibitor AR-42 in the Treatment of Cancer-Induced Cachexia//JNCI J Natl Cancer Inst (2015) 107(12)).

The day of the injection of tumor cells was taken as Day 1 of the experiment. Treamid was administered at a dose of 10 mg/kg intragastrically once daily, every day from Day 15 to Day of the study. The animals were weighed one day before the introduction of tumor cells (Day 0) and on Day 28 of the experiment. On Day 28, the animals were euthanized in a $CO_2$ chamber, and blood was collected. The level of free testosterone was determined in the blood serum by enzyme immunoassay.

The results of the study showed that the weight of animals on Day 28 after the Lewis lung carcinoma lavage (pathological control), including the subtraction of the weight of the primary tumor node, significantly decreased, by 1.2 times, compared to that in the group of healthy animals (Table 38). Intragastric administration of Treamid completely prevented the loss of body weight of the animals with Lewis lung carcinoma (Table 38).

TABLE 38

The body weight of male C57Bl/6 mice with cachexia induced by Lewis lung carcinoma, taking into account the subtraction of the primary tumor node (d) on Day 28 of the experiment (M ± m, n = 10)

| Group | Body weight, including the subtraction of the tumor weight |
|---|---|
| Intact control | 23.95 ± 0.39 |
| Lewis lung carcinoma | 20.44 ± 0.88* |
| Lewis lung carcinoma, treated with Treamid (10 mg/kg) | 23.83 ± 0.57• |

Notes:
*differences are significant vs. intact control (P < 0.05);
•differences are significant vs. pathological control (Lewis lung carcinoma) (P < 0.05).

Immunoenzymatic analysis of the blood serum showed that the serum testosterone level markedly decreased (up to 14.8% of the intact control) in the pathological control animals with Lewis lung carcinoma on Day 28 of the study (Table 39). The course administration of Treamid significantly increased the concentration of free testosterone in animal serum with LLC.

TABLE 39

The free testosterone level (pg/ml) in the blood serum of male C57Bl/6 mice with cachexia induced by Lewis lung carcinoma on Day 28 of the experiment (M ± m, n = 10)

| Parameter | Intact control | Lewis lung carcinoma | Lewis lung carcinoma treated with Treamid (10 mg/kg) |
|---|---|---|---|
| Free testosterone | 11.36 ± 1.2 | 1.68 ± 0.22* | 3.2 ± 0.3*• |

Notes:
*differences are significant vs. intact control (P < 0.05);
•differences are significant vs. pathological control (Lewis lung carcinoma) (P < 0.05)

Thus, under the development of Lewis lung carcinoma, oral administration of Treamid prevented the development of cachexia. The therapeutic effect of Treamid is due to the recovery of the function of muscle and testicular tissues, which was expressed in the recovery of the free testosterone serum level in the affected animals. This allows the conclusion that Treamid can be used as a drug that prevents the development of cachexia.

Example 40

Pharmaceutical Composition

| Composition per tablet, mg | | |
|---|---|---|
| Component | mg | mg |
| Treamid (active agent) | 5.00 | 50.00 |
| Additives: | | |
| Microcrystalline cellulose (NF, Ph. Eur., JP) | 60.00 | 300.00 |
| Pregelatinized starch (Ph. Eur., USP, NF) | 27.80 | 114.00 |
| Sodium carboxymethyl starch (Ph. Eur., NF, JP) | 4.00 | 20.00 |
| Talc (Ph. Eur., USP, JP) | 2.00 | 10.00 |
| Magnesium stearate (USP, NF) | 1.00 | 5.00 |
| Silicon dioxide, colloidal | 0.20 | 1.00 |
| Film coating Opadry ®II 31F280007 | 3.00 | 15.00 |
| Coated tablet weight | 103.00 | 515.00 |

The inventor has found that Treamid promotes tissue regeneration and normalization of the structure of prostate tissue on the models of chronic abacterial prostatitis (CAP) and benign prostatic hyperplasia (BPH). The obtained data allow the conclusion that the use of Treamid promotes the regeneration of the prostate epithelial tissue. This is expressed in a decrease in the severity of atrophic processes. The latter, obviously, will lead to an increase in the functional activity of the acinar epithelium and will promote restoration of qualitative characteristics of the ejaculate.

The applicant also experimentally in vivo demonstrated that in administration of Treamid, the symptoms of BPH were less pronounced. These data confirm antiproliferative properties of Treamid.

Further, the inventor has found that Treamid is an agent that enhances the processes of reparative regeneration of testicular tissue and can be used in the treatment of testicular failure caused by depletion of the proliferative pool of spermatogenesis.

The obtained data demonstrate that Treamid has the ability to directly stimulate the functional activity of progenitor cells for spermatogenic tissue.

In addition, the applicant has experimentally confirmed that Treamid is a potential agent for recovery of the regenerative potential of the testis. The administration of Treamid increased the regenerative potential of the tissue. The drug not only directly stimulated the formation of new sources of proliferative pool of spermatogenesis (stem cells), but also enhanced the effect of humoral factors stimulating their formation.

The applicant also experimentally proved that Treamid restores sperm motility reduced due to administration of paclitaxel.

The data presented by the inventor show that Treamid allows effective stimulation of reparative regeneration of testicular tissue that was suppressed by a decrease in the number of committed colony-forming cells.

In addition, the Applicant showed the ability of Treamid to restore the motility of sperm cells in asthenospermia. The obtained data suggest that Treamid is an effective agent for recovery of sperm motility.

Further, the inventor has found that Treamid restores the sperm motility observed in hypogonadism.

Numerous experiments confirm that Treamid is an effective agent for recovery of copulatory activity of various etiologies (including age-related decline in activity, seasonal decline in activity, and others).

It has been shown that Treamid exerts a regenerative action on the pancreas tissue. Treamid can be used to treat impaired glucose tolerance and metabolic syndrome.

It has also been experimentally shown that Treamid can be used as a drug that restores the structural and functional characteristics of liver tissue.

In addition, it has been demonstrated that Treamid can be used as a drug that restores the structural and functional characteristics of cancer tissue.

What is claimed is:

1. A method for treating structural or functional damage of a tissue selected from the group consisting of a pancreatic tissue, a liver tissue, a lung tissue, a muscular tissue, a spermatogenic tissue, a testicular tissue, and a prostate tissue, the method comprising administering to a subject in need thereof an effective amount of a compound of formula (I):

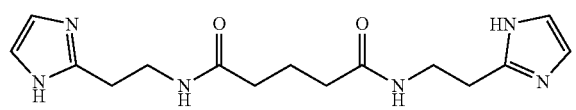 [SMILES: O=C(CCCC(=O)NCCc1ncc[nH]1)NCCc1ncc[nH]1]

or a pharmaceutically acceptable salt thereof.

2. The method of claim 1, wherein a pathological condition is associated with the structural or functional damage, said pathological condition selected from the group consisting of metabolic syndrome, glucose tolerance failure, hepatitis, idiopathic pulmonary fibrosis, pulmonary emphysema, chronic obstructive pulmonary disease, cachexia, hypogonadism, prostatitis, benign prostatic hyperplasia, correlative testicular failure, and autoimmune orchitis.

3. The method of claim 2, wherein the prostatitis is chronic prostatitis, in particular abacterial chronic prostatitis; or category 3B prostatitis, or autoimmune prostatitis.

4. A method for recovery of liver structure and function in the treatment and/or prevention of a pathological condition, the method comprising administering to a subject in need thereof an effective amount of a compound of formula (I):

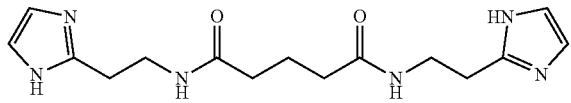 [SMILES: O=C(CCCC(=O)NCCc1ncc[nH]1)NCCc1ncc[nH]1]

or a pharmaceutically acceptable salt thereof, and a pharmaceutically acceptable carrier.

5. The method of claim 4, wherein the pathological condition is hepatitis, in particular chronic hepatitis and toxic hepatitis.

6. A method for recovery of lung structure and function in the treatment and/or prevention of a pathological condition, the method comprising administering to a subject in need thereof an effective amount of a compound of formula (I):

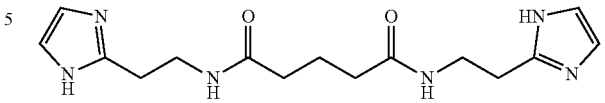

or a pharmaceutically acceptable salt thereof, and a pharmaceutically acceptable carrier.

7. The method of claim 6, wherein the pathological condition is selected from the group consisting of chronic obstructive pulmonary disease (COPD), pulmonary emphysema, and idiopathic pulmonary fibrosis.

8. A method for recovery of pancreas structure and function in the treatment and/or prevention of a pathological condition, the method comprising administering to a subject in need thereof an effective amount of a compound of formula (I):

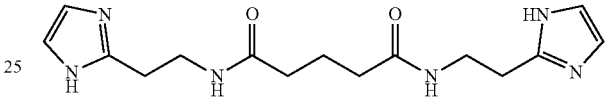

or a pharmaceutically acceptable salt thereof, and a pharmaceutically acceptable carrier.

* * * * *